US010145946B2

(12) United States Patent
Kashima et al.

(10) Patent No.: US 10,145,946 B2
(45) Date of Patent: Dec. 4, 2018

(54) GENERATING A TOMOGRAPHIC IMAGE BASED ON SENSOR INFORMATION

(71) Applicant: Sony Corporation, Tokyo (JP)

(72) Inventors: Koji Kashima, Kanagawa (JP); Tatsumi Sakaguchi, Kanagawa (JP); Takeshi Miyai, Kanagawa (JP); Hiroshi Kajihata, Tokyo (JP)

(73) Assignee: Sony Corporation, Tokyo (JP)

(*) Notice: Subject to any disclaimer, the term of this patent is extended or adjusted under 35 U.S.C. 154(b) by 661 days.

(21) Appl. No.: 14/358,084

(22) PCT Filed: Nov. 22, 2012

(86) PCT No.: PCT/JP2012/080258
§ 371 (c)(1),
(2) Date: May 14, 2014

(87) PCT Pub. No.: WO2013/080871
PCT Pub. Date: Jun. 6, 2013

(65) Prior Publication Data
US 2014/0307522 A1    Oct. 16, 2014

(30) Foreign Application Priority Data
Dec. 1, 2011 (JP) .................. 2011-263642

(51) Int. Cl.
*G01S 7/00* (2006.01)
*G01S 7/52* (2006.01)
(Continued)

(52) U.S. Cl.
CPC ........ *G01S 7/52053* (2013.01); *A61B 5/6843* (2013.01); *A61B 8/4254* (2013.01);
(Continued)

(58) Field of Classification Search
USPC .......................................... 367/11
See application file for complete search history.

(56) References Cited

U.S. PATENT DOCUMENTS 6,514,205 B1 * 2/2003 Lee .................... G01S 7/52026
367/138
6,552,841 B1 * 4/2003 Lasser ................ G01N 29/0609
359/305

(Continued)

FOREIGN PATENT DOCUMENTS

JP     07-124156 A    5/1995
JP     2006-167043 A    6/2006
(Continued)

*Primary Examiner* — James R Hulka
(74) *Attorney, Agent, or Firm* — Chip Law Group

(57) ABSTRACT

An image processing device for capturing an ultrasonic image is provided with a probe to generate an ultrasonic wave and receives a reflective wave reflected at an object. A detection unit to detect one or more physical quantities of the probe. A display unit to display a tomographic image showing a cross-section of a predetermined position of the object, out of the ultrasonic image of the object. A sensor information acquisition unit to acquire a detection result by a sensor unit as sensor information. In a tomographic image generation unit, regarding the sensor information as a parameter, a reference tomographic image is transformed according to a change of the parameter, to generate the tomographic image. A display control unit to control the display unit to display the generated tomographic image. The present technique can be applied to an ultrasonic examination device.

16 Claims, 17 Drawing Sheets

(51) Int. Cl.
   *A61B 8/08*   (2006.01)
   *A61B 5/00*   (2006.01)
   *G01S 15/02*  (2006.01)
   *A61B 8/00*   (2006.01)
   *A61B 8/14*   (2006.01)

(52) U.S. Cl.
   CPC .............. *A61B 8/462* (2013.01); *A61B 8/465* (2013.01); *A61B 8/5292* (2013.01); *G01S 15/02* (2013.01); *A61B 8/14* (2013.01); *A61B 8/4245* (2013.01); *A61B 8/466* (2013.01); *A61B 8/483* (2013.01)

(56) References Cited

U.S. PATENT DOCUMENTS

| | | | | |
|---|---|---|---|---|
| 8,777,855 | B2* | 7/2014 | Hyun | A61B 8/12 382/131 |
| 2007/0073148 | A1 | 3/2007 | Kim | |
| 2007/0205373 | A1* | 9/2007 | Kornblau | A61B 19/52 250/390.12 |
| 2008/0001945 | A1* | 1/2008 | Kashito | G11B 27/034 345/418 |
| 2008/0074531 | A1* | 3/2008 | Ide | G03B 3/00 348/346 |
| 2008/0303898 | A1* | 12/2008 | Nishimura | A61B 1/0005 348/65 |
| 2009/0124903 | A1* | 5/2009 | Osaka | A61B 8/12 600/443 |
| 2009/0127459 | A1* | 5/2009 | Neustadter | A61B 19/52 250/336.1 |
| 2009/0244097 | A1* | 10/2009 | Estevez | G06F 1/1613 345/633 |
| 2009/0275837 | A1* | 11/2009 | Shiina | A61B 5/0048 600/459 |
| 2011/0040186 | A1* | 2/2011 | Matsumura | A61B 5/6843 600/443 |
| 2011/0040187 | A1* | 2/2011 | Matsumura | A61B 5/6843 600/443 |
| 2011/0046478 | A1* | 2/2011 | Kornblau | A61B 19/52 600/424 |
| 2011/0149096 | A1* | 6/2011 | Matsuyama | H04N 5/23248 348/208.6 |
| 2011/0198510 | A1* | 8/2011 | Neustadter | A61B 19/52 250/394 |
| 2011/0301465 | A1* | 12/2011 | Waki | A61B 8/08 600/445 |
| 2012/0130244 | A1* | 5/2012 | Kim | A61B 8/461 600/443 |
| 2012/0220873 | A1* | 8/2012 | Hyun | A61B 8/12 600/443 |

FOREIGN PATENT DOCUMENTS

| | | |
|---|---|---|
| JP | 2007-075589 A | 3/2007 |
| JP | 2009-000148 A | 1/2009 |
| JP | 2011-143078 A | 7/2011 |
| JP | 2011-152356 A | 8/2011 |

* cited by examiner

FIG. 1
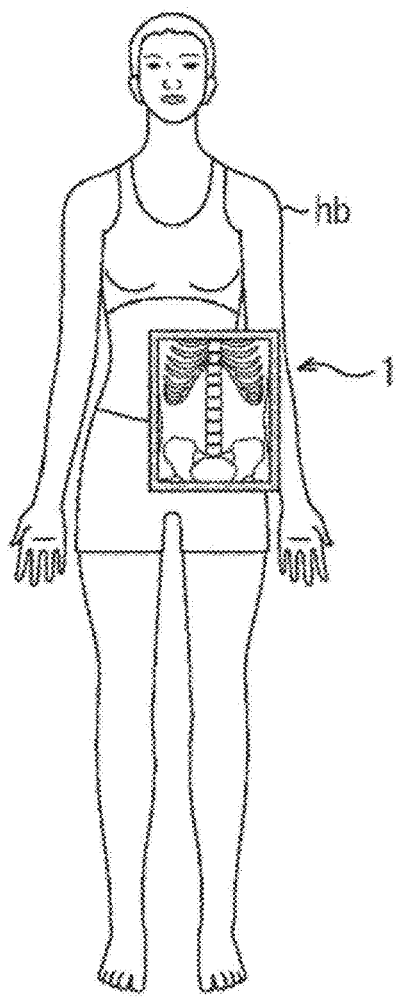
A
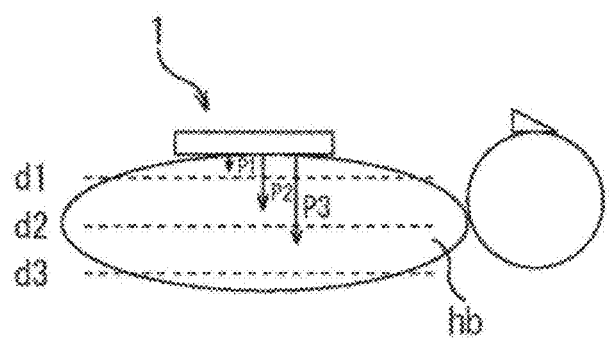
B

GENERATING A TOMOGRAPHIC IMAGE BASED ON SENSOR INFORMATION

TECHNICAL FIELD

The present technique relates to an image processing device, an image processing method, and a program, and particularly to an image processing device, an image processing method, and a program capable of grasping an ultrasonic image with an intuitive and simplified operation.

BACKGROUND ART

In a medical field, the following has been widely performed in recent years: an examination (hereinafter, referred to as an ultrasonic examination) that uses a device for imaging an ultrasonic image of a body organ or the like (hereinafter referred to as an ultrasonic image device). Specifically, the ultrasonic image device includes a probe and a display. A doctor or the like checks the ultrasonic image of an object to be examined, such as an organ displayed on the display, while pressing the probe against a subject's body to make the ultrasonic examination (see, for example, Patent Document 1).

CITATION LIST

Patent Document

Patent Document 1: JP 2011-152356 A

SUMMARY OF THE INVENTION

Problems to be Solved by the Invention

However, in an ultrasonic image device of the related art, a probe and a display are physically separated and configured individually. Therefore, a doctor or the like views a subject's body on which the probe is pressed and the display on which an ultrasonic image of an object to be examined is displayed alternately to check an examination process, while facing the display. As a result, the doctor or the like has to busily look at various positions. Thus, substantial effort is required for an ultrasonic examination.

Even in the ultrasonic image device of the related art, if a predetermined operation is performed to a controller physically separated from the probe and the display, it is at least possible to display, on the display, the ultrasonic image showing a cross-section of any position in the body (hereinafter referred to as a tomographic image). However, the doctor or the like has to perform many complicated operations to the controller to display the tomographic image of a desired position in the body. Note that it is difficult for the doctor or the like to intuitively grasp an imaging position in the body by merely simplifying many operations.

The present technique has been invented under such circumstances, and allows the grasp of an ultrasonic image with an intuitive and simplified operation.

Solutions to Problems

An image processing device according to one aspect of the present technique includes a probe, a sensor unit, a display unit, a tomographic image generation unit, and a display control unit. The probe generates an ultrasonic wave and receives a reflective wave reflected at an object. The sensor unit detects one or more physical quantities of the probe. The display unit displays the tomographic image showing a cross-section of a predetermined position of the object based on the reflective wave received by the probe. In the tomographic image generation unit, regarding sensor information detected by the sensor unit as a parameter, a reference tomographic image is transformed according to a change of the parameter, whereby the tomographic image to be displayed on the display unit is generated. The display control unit controls the display unit to display the tomographic image generated by the tomographic image generation unit.

The tomographic image generation unit may use at least a part of the sensor information as an input parameter to calculate a predetermined function, obtain accordingly at least one of variable elements of a depth, a rotation angle, and a zoom ratio of the tomographic image, and transform the reference tomographic image by use of the variable element to generate the tomographic image to be displayed.

The sensor unit may detect pressure applied by the probe as the sensor information. The tomographic image generation unit may associate a change of the pressure with a change in the depth from the predetermined position of the object to generate the tomographic image.

The tomographic image generation unit may generate the tomographic image such that the stronger the pressure of the probe, the deeper the depth of the tomographic image from the predetermined position of the object.

The sensor unit may detect a rotation angle of the probe as the sensor information. The tomographic image generation unit may associate a change in the rotation angle with the rotation angle and/or the zoom ratio of the tomographic image to generate the tomographic image.

As the rotation angle, the sensor information may include each rotation angle of an X axis, a Y axis, and a Z axis. The tomographic image generation unit may associate a change in the rotation angle of the X axis with the rotation angle of the X axis of the tomographic image, associate a change in the rotation angle of the Y axis with the rotation angle of the Y axis of the tomographic image, and associate a change in the rotation angle of the Z axis with the zoom ratio of the tomographic image to generate the tomographic image.

The tomographic image generation unit may generate the tomographic image such that the larger the rotation angle of the X axis or the rotation angle of the Y axis, the larger the rotation angle of the tomographic image.

The tomographic image generation unit may generate the tomographic image such that the larger the rotation angle of the Z axis, the larger the zoom ratio of the tomographic image.

The tomographic image generation unit may obtain information on a touch operation on a touch panel as the parameter, and transform the reference tomographic image by associating the transformation with the change of the parameter to generate the tomographic image to be displayed on the display unit.

An image processing method according to one aspect of the present technique corresponds to the image processing device according to one aspect of the present technique described above.

A program according to one aspect of the present technique corresponds to the image processing device according to one aspect of the present technique described above.

In the image processing device and method according to one aspect of the present technique, an ultrasonic wave is generated to be reflected at an object, the thus obtained reflective wave is received, one or more physical quantities is detected, the tomographic image showing the cross-section of the predetermined position of the object is displayed based on the received reflective wave, and the tomographic image to be displayed is generated by regarding detected sensor information as the parameter and transforming a reference tomographic image according to the change of the parameter.

EFFECTS OF THE INVENTION

As has been described, according to the present technique, it is possible to grasp an ultrasonic image with an intuitive and simplified operation.

BRIEF DESCRIPTION OF DRAWINGS

FIG. 1 is a diagram illustrating an outline of the present technique.

MODES FOR CARRYING OUT THE INVENTION

[Outline of Present Technique]

Figure 2:
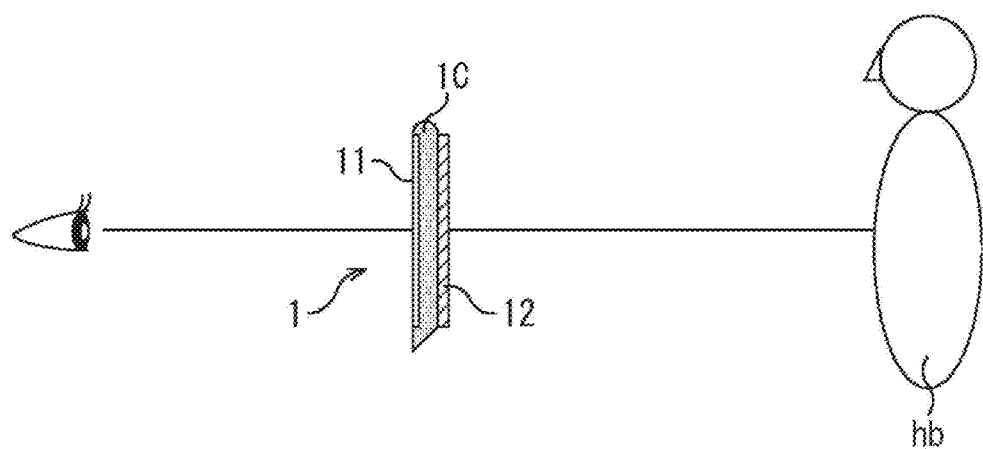
FIG. 2 is a diagram illustrating a positional relationship among an examiner, an image processing device, and a body.

First, an outline of the present technique is described to make understanding of the present technique easy.

FIG. 1 is a diagram illustrating an outline of the present technique. An image processing device 1 to which the present technique is applied is an ultrasonic image device obtained by integrating a display unit such as a display, and a probe. The image processing device is used for an ultrasonic examination in a medical field, for example. Note that, among surfaces of the image processing device 1, a surface to which the display unit is provided is called a front surface, and a surface which is opposite to the front surface and to which the probe is provided is called a back surface. Also note that, for simplifying the description below, a direction from the front surface to the back surface of the image processing device 1 is called a downward direction, and reversely, a direction from the back surface to the front surface of the image processing device 1 is called an upward direction, based on the presumption that the image processing device 1 can be placed in any position.

As illustrated in FIG. 1A, during the ultrasonic examination, the back surface, to which the probe is provided, of the image processing device 1 is pressed against a predetermined position on the surface of a body hb of a subject, in other words, a position immediately above an object to be examined, such as an organ. At this time, the display unit provided to the front surface of the image processing device 1 displays, in real time, a tomographic image showing a cross-section of any position of the object to be examined. Thus, the doctor or the like who performs the ultrasonic examination (hereinafter referred to as an examiner) views the tomographic image of the object to be examined displayed on the display unit, from immediately above the front surface of the image processing device 1. In this manner, the examiner can have a sense as if viewing inside the body hb over the display unit of the image processing device 1.

Further, as illustrated in FIG. 1B, the examiner may change a level of pressing force applied to the body hb by the image processing device 1 to change a depth (in other words, a distance from the back surface of the image processing device 1) of a position in the body which is shown in the tomographic image as the object to be examined. Specifically, if pressure P of the image processing device 1 applied by the examiner to the body hb becomes stronger in order of pressures P1, P2, and P3, the depth from the surface of the body hb displayed on the display unit as the tomographic image increases in order of depths d1, d2, and d3. In this manner, according to the intensity of the pressure P, the depth position from the surface of the body hb displayed on the display unit as the tomographic image increases.

Alternatively, although the detail will be described later, the examiner may change an angle (hereinafter simply referred to as the angle of the image processing device 1) formed between the back surface (in other words, the probe) of the image processing device 1 pressed against the body hb and the surface of the body hb to thereby change a virtual viewpoint for imaging inside the body hb. In other words, according to a change of the angle of the image processing device 1, the virtual viewpoint also changes. In this manner, the display unit of the image processing device 1 displays the tomographic image showing inside the body hb imaged from the virtual viewpoint according to the angle of the image processing device 1.

Further alternatively, the examiner may rotate the image processing device 1 while pressing the image processing device 1 against the body hb. Accordingly, the display unit is allowed to display the zoomed-in or zoomed-out tomographic image.

[Positional Relationship Among Examiner, Image Processing Device 1, and Body hb]

FIG. 2 is a diagram illustrating the positional relationship among the examiner, the image processing device 1, and the body hb.

The image processing device 1 is configured by integrating a display unit 11 and a probe 12. Note that the display unit 11 is provided at a front surface of a housing 1C of the image processing device 1. In other words, more specifically, in the present embodiment, the probe 12 is provided at the back surface of the housing 1C. Thus, the display unit 11 is integrally provided with the probe 12.

As illustrated in FIG. 2, the image processing device 1 is arranged such that a visual line of an examiner, a normal line of a display surface of the display unit 11, a radiation direction of an ultrasonic wave of the probe 12, and a direction nearly vertical to the front surface of the body hb of a subject are aligned nearly on a straight line. Note that, in practice, the probe 12 is in contact with the front surface of the body hb.

By arranging the image processing device 1 in this manner, for an observation purpose, the examiner can cause the display unit 11 to display an ultrasonic image of an object to be examined which is immediately below a position of the body hb against which the probe 12 is pressed.

[Exemplary Outer Configuration]

Next, an exemplary outer configuration of the image processing device 1 is described.

Figure 3:
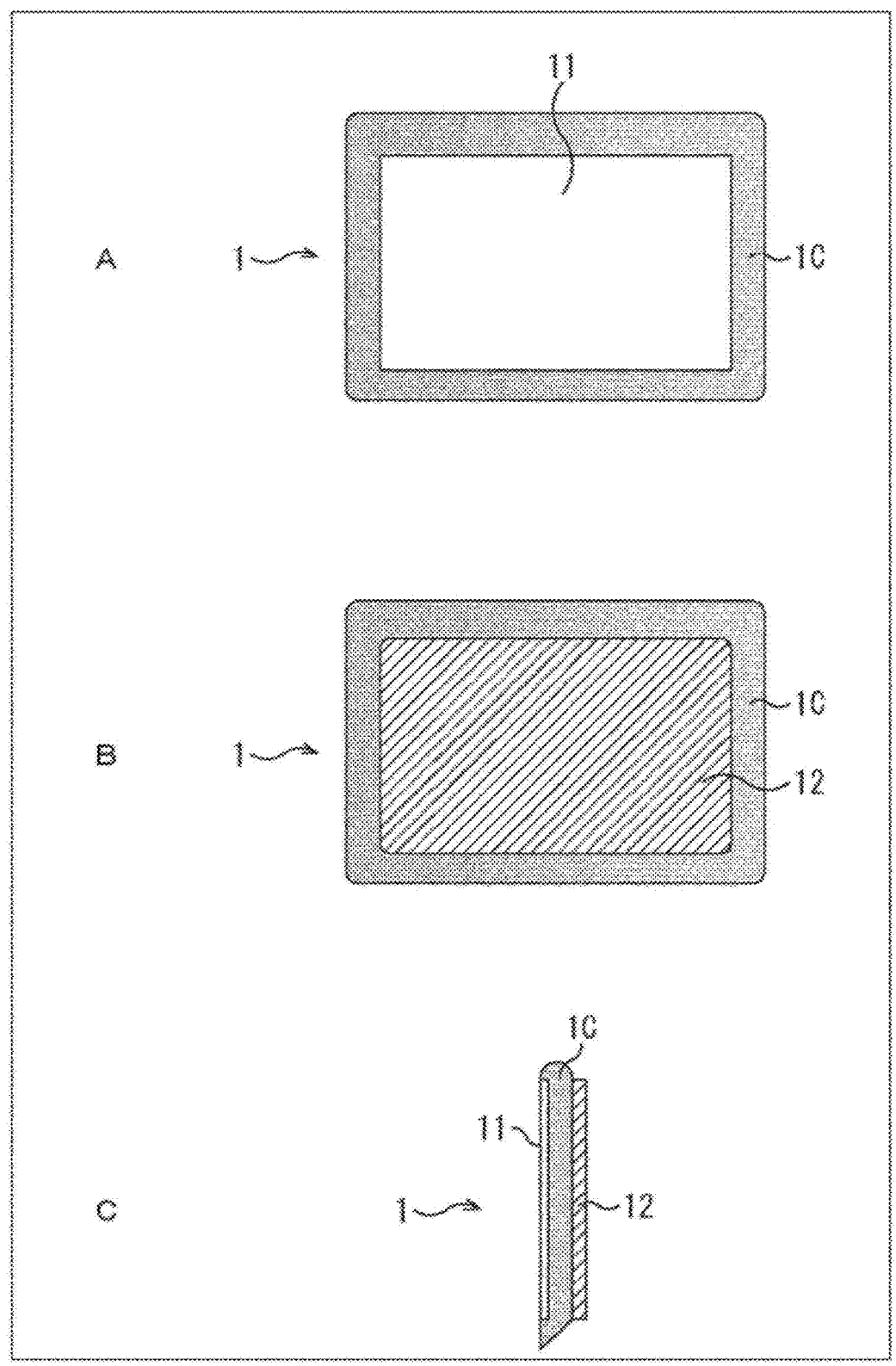
FIG. 3 is a diagram illustrating an exemplary outer configuration of the image processing device.

FIG. 3 illustrates the exemplary outer configuration of the image processing device 1, that is, in detail, a front view, a back view, and a side view.

FIG. 3A illustrates the front view of the image processing device 1. As illustrated in FIG. 3A, the display unit 11 is provided to a front surface of the image processing device 1, that is, a front surface of the housing 1C. The display unit 11 displays a tomographic image of an object to be examined inside the body hb.

Note that the display unit 11 may have a function of displaying a two-dimensional image, and further, may have a function of displaying a three-dimensional image. If the display unit 11 has the function of displaying the three-dimensional image, either a glasses technology that uses polarizing filter glasses and shutter glasses, or a naked eye system without using glasses such as a lenticular method may be adopted. The display unit 11 may have any size.

FIG. 3B is the back view of the image processing device 1. As illustrated in FIG. 3B, the probe 12 is provided to a back surface of the image processing device 1, that is, a back surface of the housing 1C. The probe 12 includes a plurality of oscillators (not shown) inside. When an ultrasonic wave is sent out from each of the plurality of oscillators, the ultrasonic wave is reflected at the object in the body hb, and a reflective wave is received by the probe 12 again. The image processing device 1 (in detail, a main control unit 51 in the housing C1 described later) processes the received reflective wave in a predetermined manner to generate data of the tomographic image of the object to be examined.

The probe 12 is used in contact with the body hb of a subject. Thus, it is preferable to use a soft and thick material allowing conduction of the ultrasonic wave for a contact surface between the probe 12 and the body hb so that imaging is possible regardless of a recess and a projection on the surface of the body hb.

Further, the oscillator in the probe 12 is not particularly limited as long as a two-dimensional plain surface can be imaged. For example, it is possible to adopt the oscillator of types, such as a two-dimensional array type and a one-dimensional array parallel moving type. Accordingly, the display unit 11 displays the tomographic image parallel to a display surface. Incidentally, if the oscillator of a one-dimensional array type is adopted as the oscillator in the probe 12, the tomographic image vertical to the display surface is displayed. Therefore, in this case, the probe 12 is manually moved in parallel to allow displaying the tomographic image of the two-dimensional plain surface.

FIG. 3C is the side view of the image processing device 1. As illustrated in FIG. 3C, the image processing device 1 is configured by integrating the housing 1C that includes the display unit 11, and the probe 12. Note that the housing 1C and the probe 12 may have any size.

[Exemplary Configuration of Image Processing Device 1]

Next, an exemplary configuration of the image processing device 1 is described.

Figure 4:
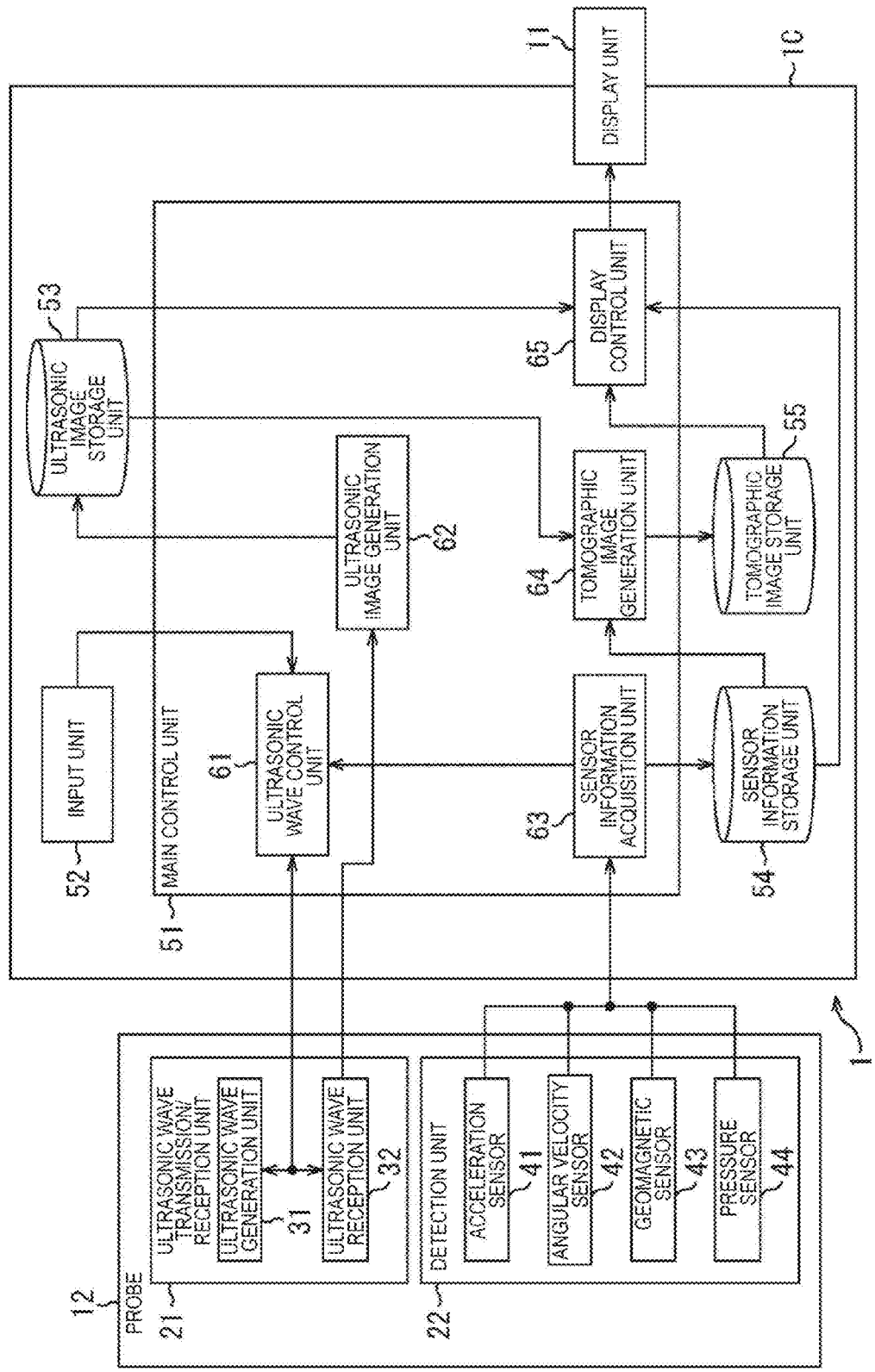
FIG. 4 is a block diagram illustrating an exemplary configuration of the image processing device to which the present technique is applied.

FIG. 4 is a block diagram illustrating the configuration example of the image processing device 1 to which the present technique is applied.

As described above, the image processing device 1 includes the display unit 11 provided to a front surface of the housing 1C, and the probe 12 provided to a back surface of the housing 1C. Specifically, the image processing device 1 includes, in its housing 1C, a main control unit 51, an input unit 52, an ultrasonic image storage unit 53, a sensor information storage unit 54, and a tomographic image storage unit 55.

The probe 12 includes an ultrasonic wave transmission/reception unit 21 and a detection unit 22.

Under the control of an ultrasonic wave control unit 61, which is described later and included in the main control unit 51, the ultrasonic wave transmission/reception unit 21 transmits/receives an ultrasonic wave. Specifically, the ultrasonic wave transmission/reception unit 21 includes an ultrasonic wave generation unit 31 and an ultrasonic wave reception unit 32.

Under the control of the ultrasonic wave control unit 61, the ultrasonic wave generation unit 31 generates an ultrasonic wave. More specifically, the ultrasonic wave generation unit 31, for example, oscillates a pulse ultrasonic wave at a predetermined interval, and scans a surface parallel to the probe 12 with the ultrasonic wave.

If the ultrasonic wave is generated by the ultrasonic wave generation unit 31 and the ultrasonic wave reflected at an object to be examined in the body hb reaches the probe 12, the ultrasonic wave reception unit 32 receives the ultrasonic wave as a reflective wave. Then, the ultrasonic wave reception unit 32 measures the intensity of the received reflective wave and feeds, to an ultrasonic image generation unit 62 described later and included in the main control unit 51, a group of data (hereinafter referred to as ultrasonic wave measurement data) obtained by arraying types of data indicating the intensity of the reflective wave in chronological order, for example.

The probe 12 that includes such ultrasonic wave transmission/reception unit 21 includes the detection unit 22 as described above. The detection unit 22 detects a condition (for example, a position, an orientation and the like) of the probe 12. In order to detect a predetermined physical quantity of the probe 12, the detection unit 22 includes an acceleration sensor 41, an angular velocity sensor 42, a geomagnetic sensor 43, and a pressure sensor 44.

The acceleration sensor 41, for example, detects the acceleration of the probe 12.

The angular velocity sensor 42 detects, for example, angular velocity in each of X, Y, and Z directions of the probe 12 to determine a tilt of the probe 12. Note that, hereinafter, an X axis is a direction (left-right direction) crossing the body hb of a subject, a Y axis is a body height direction of the subject, and a Z axis is a thickness direction of the body hb of the subject.

The geomagnetic sensor 43, for example, detects the orientation of the probe 12.

The pressure sensor 44 detects the pressure applied to the body hb by the probe 12 when the probe 12 is pressed against the body hb to take the ultrasonic image.

Incidentally, a detection result of the detection unit 22 is fed to a sensor information acquisition unit 63, which is described later and included in the main control unit 51, as sensor information.

This kind of probe 12 is controlled by the main control unit 51. Specifically, the main control unit 51 controls the entire operation of the image processing device 1 including the probe 12. In detail, the main control unit 51 includes an ultrasonic wave control unit 61, an ultrasonic image generation unit 62, a sensor information acquisition unit 63, a tomographic image generation unit 64, and a display control unit 65.

Based on an instruction operation to the input unit 52 by an examiner and each sensor information fed from the sensor information acquisition unit 63, the ultrasonic wave control unit 61 controls the ultrasonic wave generation unit 31 and the ultrasonic wave reception unit 32 included in the probe 12 to perform various operations associated with transmission/reception of the ultrasonic wave.

Based on the ultrasonic wave measurement data fed from the ultrasonic wave reception unit 32, the ultrasonic image generation unit 62 generates data of the three-dimensional ultrasonic image of the body hb positioned immediately below the area where the probe 12 is pressed, as the data of the ultrasonic image of the object to be examined, according to any publicly-known method or method to be newly found. The thus obtained data is stored in the ultrasonic image storage unit 53.

The sensor information acquisition unit 63 acquires the sensor information fed from the probe 12 to store the sensor information in the sensor information storage unit 54. At the same time, the sensor information acquisition unit 63 appropriately feeds the sensor information to the ultrasonic wave control unit 61. When the position, the orientation and the like of the probe 12 are changed, a distance from the probe 12 to an object to be examined in the body hb is also changed. Accordingly, the sensor information acquisition unit 63 feeds the sensor information to the ultrasonic wave control unit 61 so that in the probe 12 having undergone the above change, a focal point of the ultrasonic waves transmitted/received from/by the ultrasonic wave transmission/reception unit 21 is adjustable.

Based on data of the ultrasonic image stored in the ultrasonic image storage unit 53 and the sensor information stored in the sensor information storage unit 54, the tomographic image generation unit 64 generates data of the tomographic image (that is, a two-dimensional image showing a cross-section of a predetermined position in the body hb) of the object to be examined to store the data in the tomographic image storage unit 55.

Based on the data of the tomographic image stored in the tomographic image storage unit 55, the display control unit 65 controls the display unit 11 to display the tomographic image of the object to be examined. Further, the display control unit 65 controls the display unit 11 to display the sensor information stored in the sensor information storage unit 54 when necessary.

[Display Processes of Ultrasonic Examination Result]

Next, among processes executed by the image processing device 1, a description is made by referring to FIG. 5 for a series of processes (hereinafter referred to as display processes of the ultrasonic examination result) until displaying a tomographic image of an object to be examined based on sensor information as a result of the ultrasonic examination.

Figure 5:
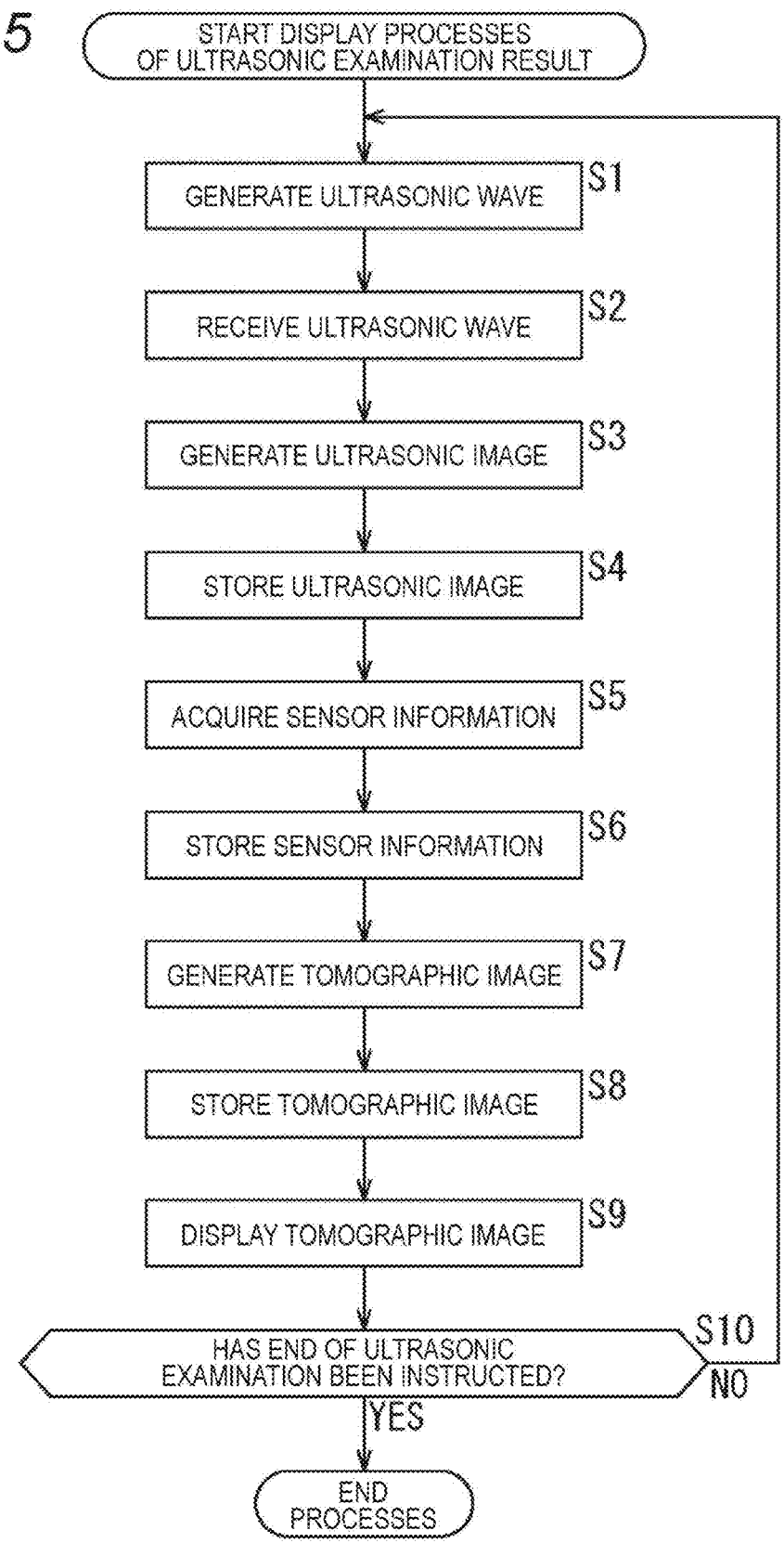
FIG. 5 is a flowchart illustrating a flow of display processes of an ultrasonic examination result.

FIG. 5 is a flowchart illustrating a flow of the display processes of the ultrasonic examination result.

The display processes of the ultrasonic examination result are started when an examiner inputs an instruction to the input unit 52 or the like to start imaging.

The ultrasonic wave generation unit 31 generates an ultrasonic wave under the control of the ultrasonic wave control unit 61 at step S1.

At step S2, under the control of the ultrasonic wave control unit 61, the ultrasonic wave reception unit 32 receives a reflective wave of the ultrasonic wave generated by the ultrasonic wave generation unit 31. Then, the ultrasonic wave reception unit 32 measures the intensity of the received reflective wave to feed, to the ultrasonic image generation unit 62, ultrasonic wave measurement data indicating a measurement result.

Based on the ultrasonic wave measurement data fed from the ultrasonic wave reception unit 32, at step S3, the ultrasonic image generation unit 62 generates data of a three-dimensional ultrasonic image of the body hb positioned immediately below the probe 12.

At step S4, the ultrasonic image generation unit 62 stores the generated data of the ultrasonic image in the ultrasonic image storage unit 53.

At step S5, the sensor information acquisition unit 63 acquires the sensor information fed from each sensor of the probe 12.

At step S6, the sensor information acquisition unit 63 stores the acquired sensor information in the sensor information storage unit 54.

Based on the data of the three-dimensional ultrasonic image read from the ultrasonic image storage unit 53 and the sensor information read from the sensor information storage unit 54, at step S7, the tomographic image generation unit 64 generates the data of the two-dimensional tomographic image showing the object to be examined viewed from a predetermined virtual viewpoint. Specifically, first, the tomographic image generation unit 64 generates reference data of the tomographic image. Then, the tomographic image generation unit 64 calculates a predetermined function by presuming the acquired sensor information as an input parameter. Accordingly, at least one of variable elements of a depth of a viewpoint, a rotation angle, and a zoom ratio of the tomographic image is obtained. Thereafter, the tomographic image generation unit 64 transforms reference data based on a predetermined algorithm by use of the element to generate the data of the tomographic image. That is, when the depth of the viewpoint, the rotation angle, or the zoom ratio of the tomographic image is changed, the data of the tomographic image to be generated also changes. A method for generating the data of the tomographic image is described later.

The tomographic image generation unit 64 stores the generated data of the tomographic image in the tomographic image storage unit 55 at step S8.

The display control unit 65 displays the tomographic image at step S9. Specifically, the display control unit 65 reads the data of the tomographic image from the tomographic image storage unit 55 and controls the display unit 11 to display the tomographic image based on the read data of the tomographic image.

The input unit 52 determines at step S10 whether an end of the ultrasonic examination has been instructed.

If the end of the ultrasonic examination has not been instructed (NO in step S10), the process returns to step S1 to repeat step S1 and the subsequent processes. That is, until the end of the ultrasonic examination is instructed, loop processes from step S1 to step S10 are repeated.

Thereafter, if the end of the ultrasonic examination is instructed (YES in step S10), the display processes of the ultrasonic examination result are ended.

[Relationship Between Pressure and Tomographic Image]

Further, hereinafter, among the display processes of an ultrasonic examination result, a process at step S7 is specifically described. Specifically, a method for generating data of a tomographic image at a process of step S7 is described in detail.

Figure 6:
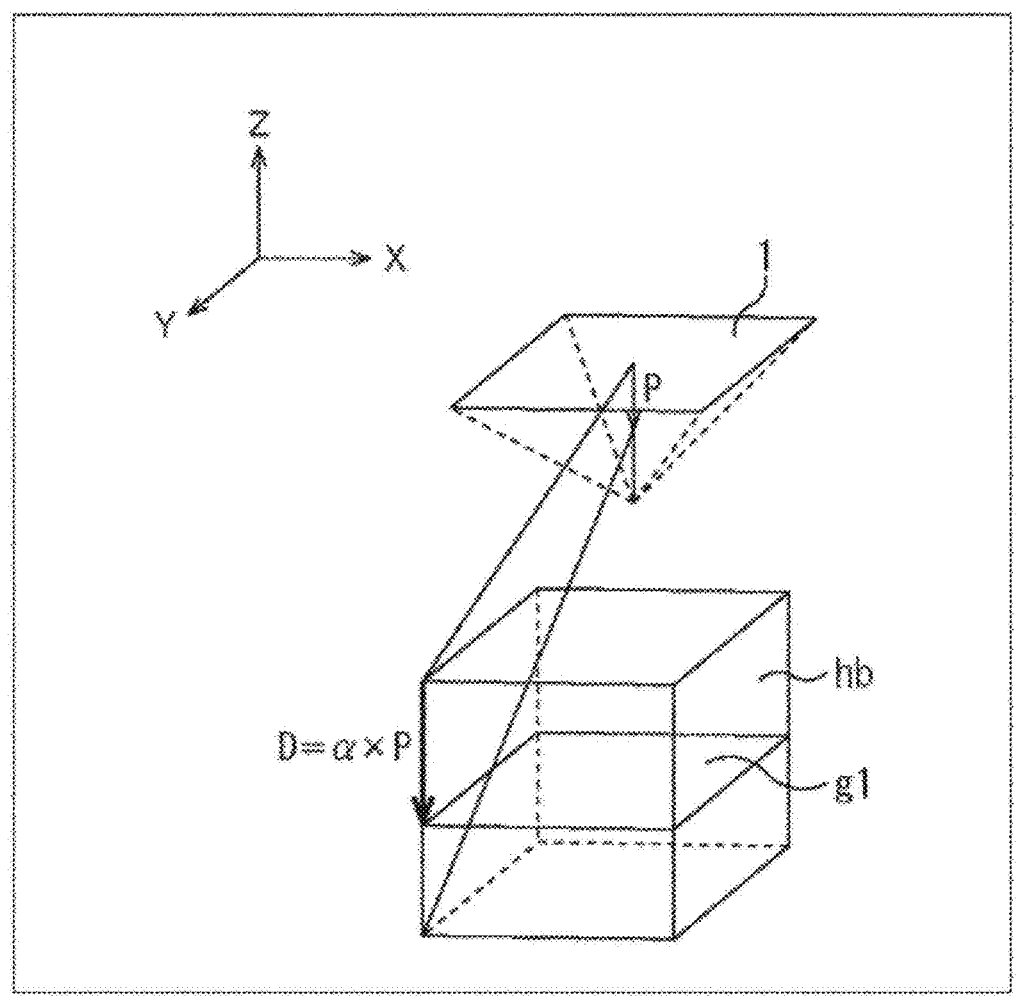
FIG. 6 is a diagram illustrating a relationship between pressure and a depth of a viewpoint of a tomographic image.

FIG. 6 is a diagram illustrating a relationship between pressure P applied to the body hb by the image processing device 1 and a depth of a viewpoint of a tomographic image. Herein, presuming the presence of a virtual viewpoint in an upward direction from a surface of the body hb, the depth of the viewpoint of the tomographic image means a distance in the vertical direction (herein, a Z direction) from the virtual viewpoint to a position of an object to be examined (a cross-section) shown in the tomographic image.

As illustrated in FIG. 6, when the predetermined pressure P is applied to the body hb in a Z axis direction by the image processing device 1, a depth D of the viewpoint of a tomographic image g1 displayed on the display unit 11 is represented by, for example, the following formula (1).

$$D = \alpha \times P \quad (1)$$

In the formula (1), a coefficient $\alpha$ is a parameter for adjustment and an examiner can freely set and change the coefficient.

The sensor information acquisition unit 63 acquires sensor information that includes a detection result of the pressure sensor 44 included in the detection unit 22 and stores the sensor information in the sensor information storage unit 54. Then, the tomographic image generation unit 64 substitutes the detection result of the pressure sensor 44 stored in the sensor information storage unit 54 for the pressure P which is an input parameter of the formula (1) to calculate the formula (1). Thus, the depth D of the viewpoint of the tomographic image is acquired. Accordingly, the tomographic image generation unit 64 generates the data of the tomographic image that shows inside the body hb at the position of the calculated depth D of the viewpoint of the tomographic image. In this manner, the tomographic image generation unit 64 can generate the tomographic image data in which the depth D of the viewpoint is changed according to the intensity of the pressure P.

Herein, the tomographic image generation unit 64 multiplies variation of the pressure P applied to the body hb by the image processing device 1 by $\alpha$ times to acquire the depth D of the viewpoint of the tomographic image. That is, even though a change in the pressure P is small, the small change is amplified by $\alpha$ times. Thus, the change in the depth D of the viewpoint of the tomographic image becomes large.

Figure 7:
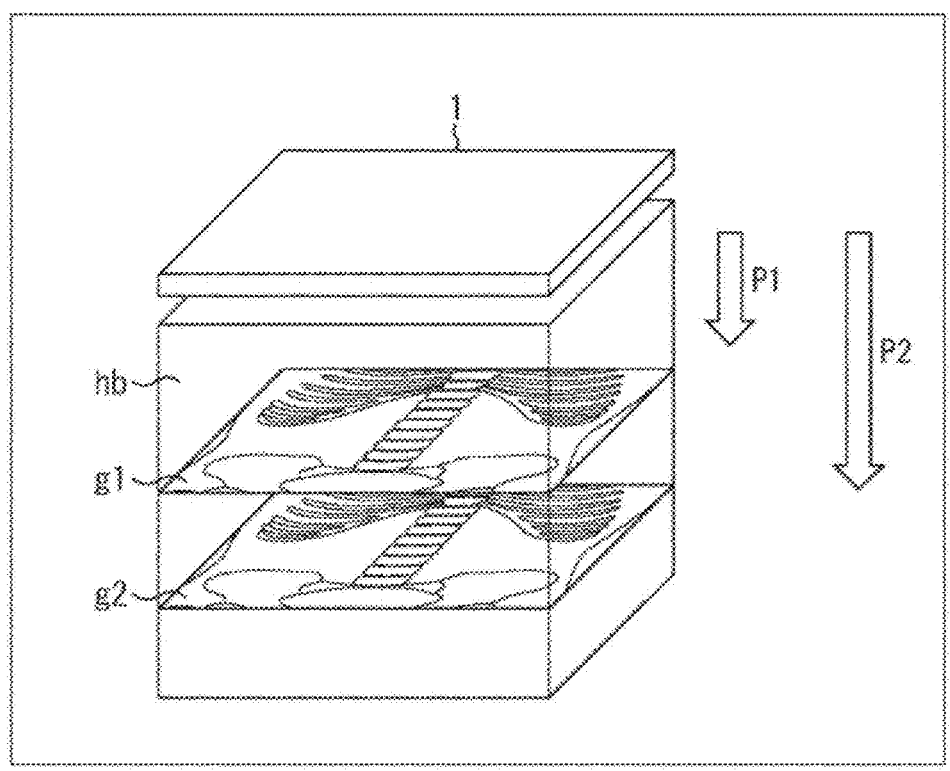
FIG. 7 is a diagram specifically illustrating a process result.

FIG. 7 is a diagram specifically illustrating a process result of FIG. 6.

As illustrated in FIG. 7, if the pressure P applied to the body hb by the image processing device 1 is pressure P1, the display unit 11 displays the tomographic image g1 of a position nearer to a surface. Further, if the pressure P applied to the body hb by the image processing device 1 is pressure P2, which is stronger than the pressure P1, the display unit 11 displays a tomographic image g2 whose depth D of the viewpoint is deeper than that of the tomographic image g1.

When the image processing device 1 is pressed against a predetermined position of the body hb, that position may be a painful area. In this case, if the pressure P applied to the body hb by the image processing device 1 is too strong, there is a possibility that a subject may suffer from a pain. Further, if the pressure P applied to the body hb by the image processing device 1 is too strong, the body hb's position where the image processing device 1 is pressed may be deformed. In this case, there is a possibility that an ultrasonic examination cannot be made precisely. Therefore, as described above, even if the pressure P applied to the body hb by the image processing device 1 is small, the depth D of the viewpoint is arranged to be large.

[Relationship Between Angle of Rotating about X Axis and Tomographic Image]

Next, the relationship between the angle of pressing the image processing device 1 against the body hb and the tomographic image is described.

Figure 8:
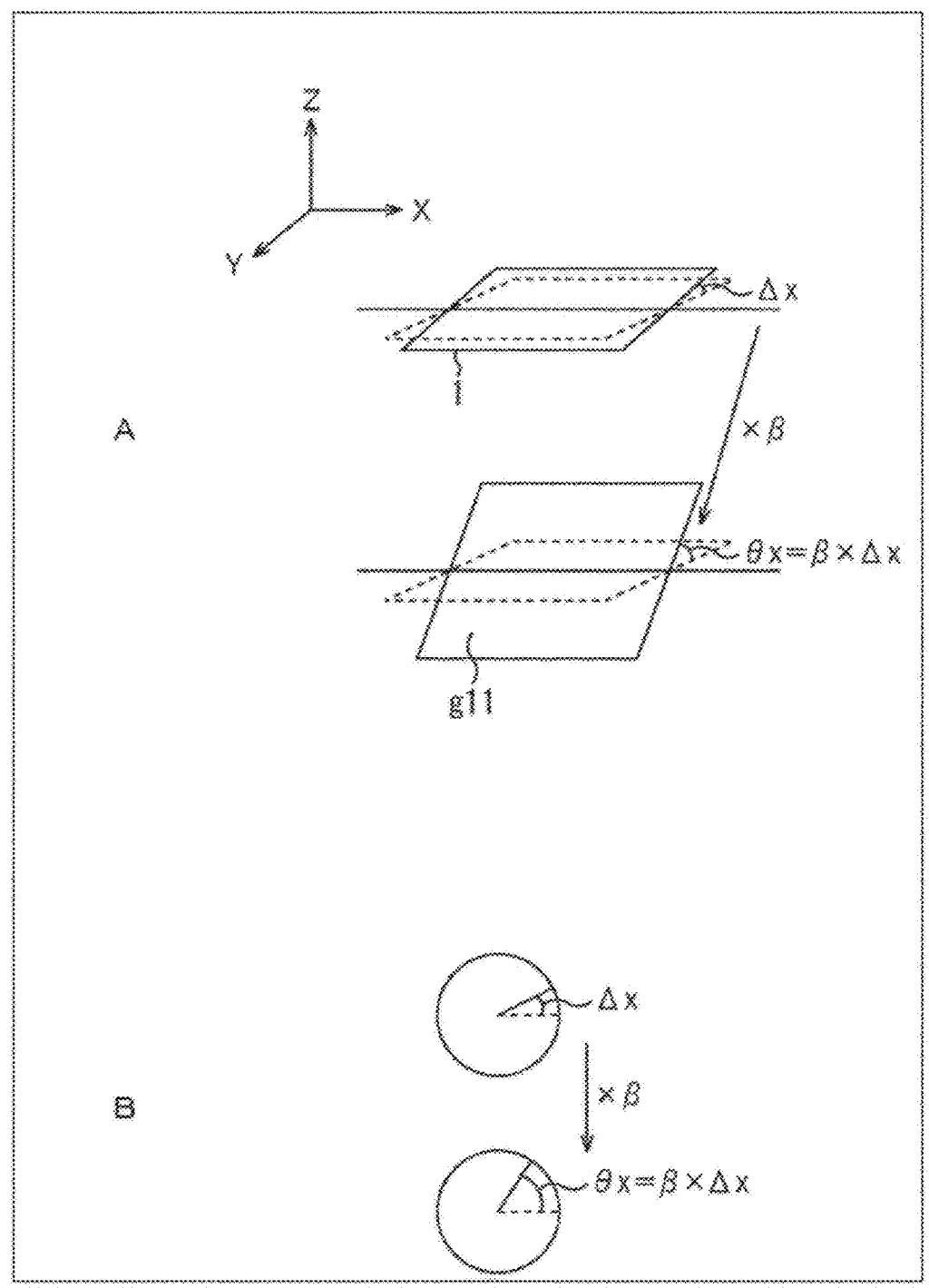
FIG. 8 is a diagram illustrating a relationship between an angle of rotating about an X axis and the tomographic image.

FIG. 8 is a diagram illustrating the relationship between an angle of rotating the image processing device 1 about an X axis and a tomographic image.

Herein, if the probe 12 provided to a back surface of the image processing device 1 is arranged at a predetermined position parallel to an XY plain surface, such condition is called a reference condition. Further, the tomographic image taken with the image processing device 1 in the reference condition is called a reference tomographic image. Specifically, the tomographic image that corresponds to the above-described reference data is the reference tomographic image. Note that, a rotation angle of rotating the image processing device 1, from the reference condition, about the X axis is described as $\Delta x$.

As illustrated at an upper side of FIG. 8A, for example, it is presumed that the image processing device 1 is rotated by the rotation angle $\Delta x$ about the X axis and the thus rotated image processing device 1 is pressed against the body hb.

In this case, as illustrated at a lower side of FIG. 8A, a tomographic image g11 displayed on the display unit 11 is obtained by rotating the tomographic image about the X axis at a rotation angle $\theta x$ relative to the reference tomographic image. The rotation angle $\theta x$ is obtained by amplifying the actual rotation angle $\Delta x$ by $\beta$ times. Note that a coefficient $\beta$ is a parameter for adjustment, and an examiner can freely set and change the coefficient. FIG. 8B is a diagram schematically illustrating the rotation angle $\Delta x$ of the image processing device 1 and the rotation angle $\theta x$ of the tomographic image g11 in FIG. 8A.

The sensor information acquisition unit 63 acquires the rotation angle of the image processing device 1 as one of types of sensor information and stores the sensor information in the sensor information storage unit 54. Then, the tomographic image generation unit 64 substitutes the rotation angle about the X axis out of this rotation angle for an input parameter $\Delta x$ to calculate the following formula (2). Accordingly, the rotation angle $\theta x$ (that is, a tilt of the tomographic image) about the X axis relative to the reference tomographic image is acquired.

$$\theta x = \beta \times \Delta x \quad (2)$$

Then, the tomographic image generation unit 64 generates data of the tomographic image rotated at the rotation angle $\theta x$ about the X axis relative to the reference tomographic image, in other words, generates data of the tomographic image whose tilt is changed.

Similarly to pressing the image processing device 1 against the predetermined position of the body hb, with the image processing device 1 being tilted (rotated about the X axis), the tilting side is pressed against the body. However, the position pressed by the tilting side may be a painful area. In this case, if the rotation angle $\Delta x$ of the image processing device 1 is too large, the image processing device 1 is pressed against the body hb with a strong pressure accordingly. Thus, there is a possibility that a subject suffers from a pain. Further, if the rotation angle Δx of the image processing device 1 is too large, as a result of tilting the image processing device 1, a position of the body hb where the image processing device 1 is pressed may be deformed. In this case, there is a possibility that an ultrasonic examination cannot be performed properly. Therefore, as has been described above, even if the rotation angle Δx of the image processing device 1 is small, the rotation angle θx of the tomographic image is arranged to be large.

[Relationship Between Angle of Rotating about Y Axis and Tomographic Image]

Figure 9:
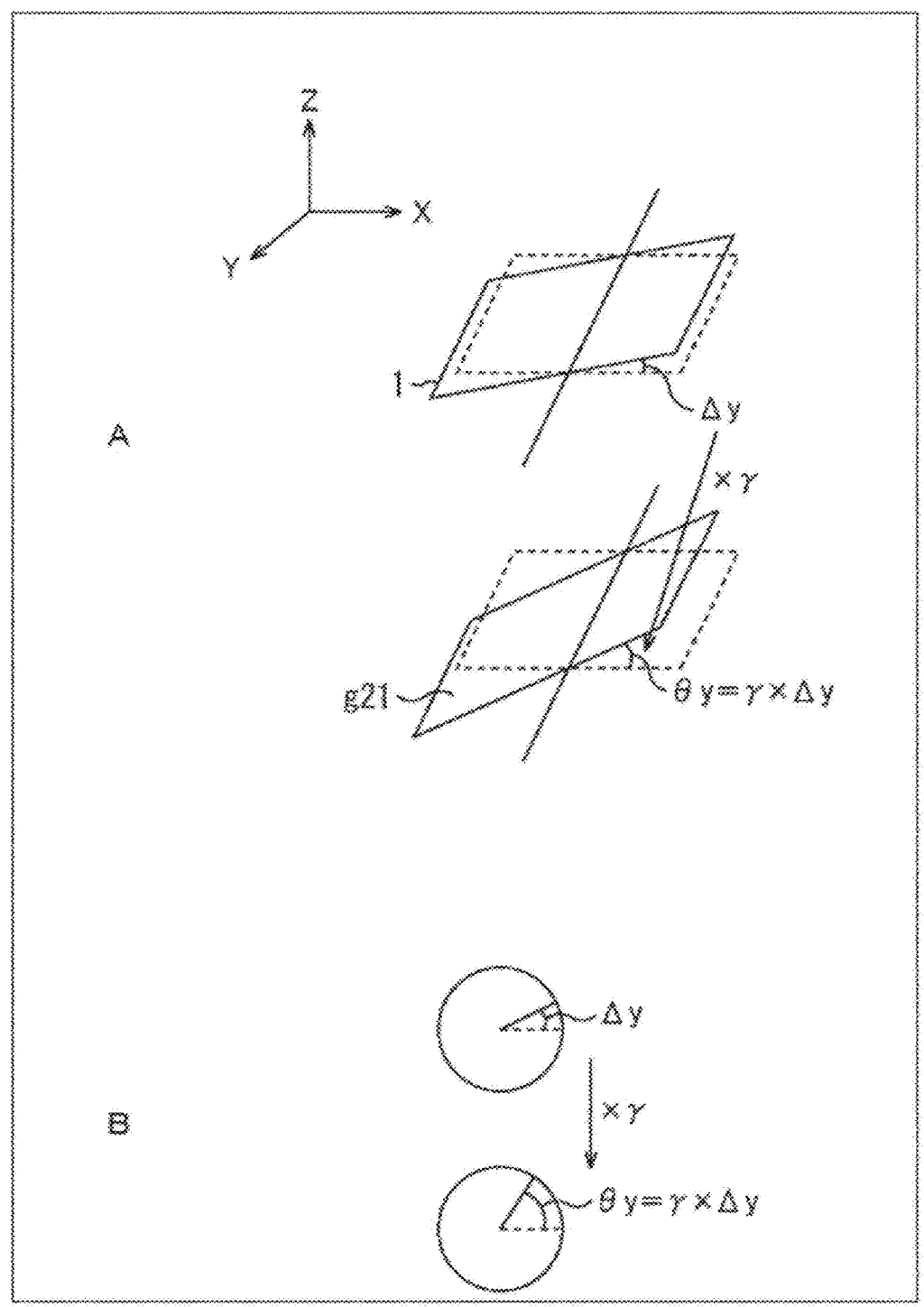
FIG. 9 is a diagram illustrating a relationship between an angle of rotating about a Y axis and the tomographic image.

FIG. 9 is a diagram illustrating the relationship between the angle of rotating the image processing device 1 about a Y axis and a tomographic image. Note that, the rotation angle of rotating the image processing device 1, from a reference condition, about the Y axis is described as Δy.

As illustrated in an upper side of FIG. 9A, for example, it is presumed that the image processing device 1 is rotated at the rotation angle Δy about the Y axis, and the thus rotated image processing device 1 is pressed against the body hb.

In this case, as illustrated at a lower side of FIG. 9A, a tomographic image g21 displayed on the display unit 11 is obtained by rotating the tomographic image about the Y axis at a rotation angle θy relative to a reference tomographic image. The rotation angle θy is obtained by amplifying the actual rotation angle Δy by γ times. Note that a coefficient γ is a parameter for adjustment, and an examiner can freely set and change the coefficient. FIG. 9B is a diagram schematically illustrating the rotation angle Δy of the image processing device 1 and the rotation angle θy of the tomographic image g21 in FIG. 9A.

The sensor information acquisition unit 63 acquires the rotation angle of the image processing device 1 as one of types of sensor information and stores the sensor information in the sensor information storage unit 54. Then, the tomographic image generation unit 64 substitutes the rotation angle about the Y axis out of this rotation angle for an input parameter Δy to calculate the following formula (3). Accordingly, the rotation angle θy (a tilt of the tomographic image) about the Y axis relative to the reference tomographic image is acquired.

$$\theta y = \gamma \times \Delta y \quad (3)$$

Then, the tomographic image generation unit 64 generates data of the tomographic image rotated at the rotation angle θy about the Y axis relative to the reference tomographic image, in other words, generates data of the tomographic image whose tilt is changed.

Similarly to pressing the image processing device 1 against the predetermined position of the body hb, with the image processing device 1 being tilted (rotated about the Y axis), the tilting side is pressed against the body. However, the position pressed by the tilting side may be a painful area. In this case, if the rotation angle Δy of the image processing device 1 is too large, the image processing device 1 is pressed against the body hb with a strong pressure accordingly. Therefore, there is a possibility that a subject suffers from a pain. Further, if the rotation angle Δy of the image processing device 1 is too large, as a result of tilting the image processing device 1, the body hb's position where the image processing device 1 is pressed may be deformed. In this case, there is a possibility that an ultrasonic examination cannot be performed properly. Therefore, as has been described above, even if the rotation angle Δy of the image processing device 1 is small, the rotation angle θy of the tomographic image is arranged to be large.

Each of the rotation angles θx and θy is obtained by tilting the image processing device 1 about the X axis or the Y axis from the reference tomographic image. Note that it is preferable that the rotation angles θx and θy be within the range of the angle from −90 degrees to 90 degrees. This is because, if the angle of a viewpoint of the tomographic image is changed within a range larger than the range of the angle from −90 degrees to 90 degrees, it becomes difficult to perform an ultrasonic examination.

Figure 10:
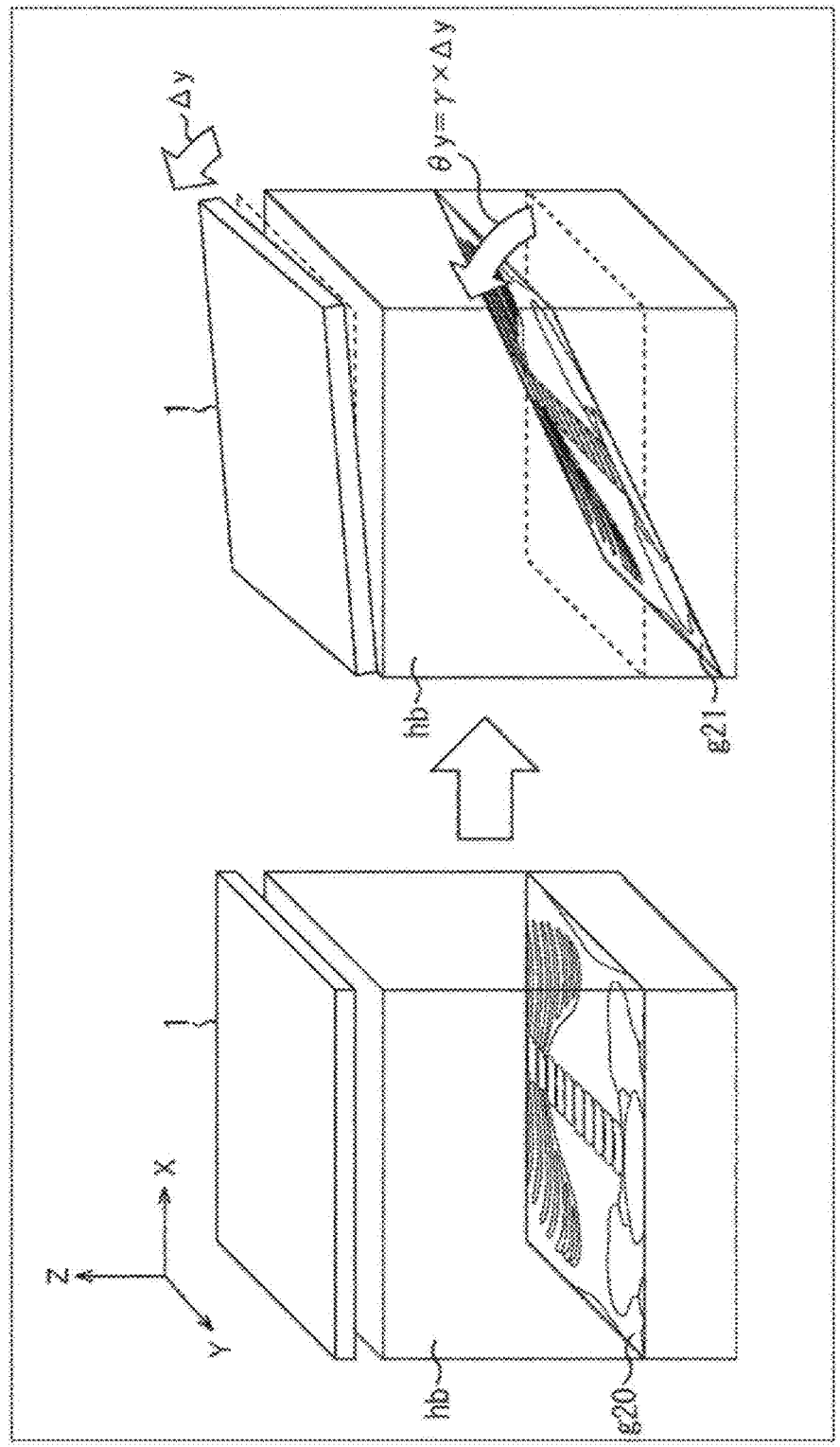
FIG. 10 is a diagram specifically illustrating a process result.

FIG. 10 is a diagram specifically illustrating a process result of FIG. 9.

As illustrated in a left side of FIG. 10, if the image processing device 1 in a reference condition is pressed against a predetermined position of the body hb, the display unit 11 displays a reference tomographic image g20.

It is presumed that, from this condition, the image processing device 1 is rotated at the rotation angle Δy about the Y axis and the thus rotated image processing device 1 is pressed against the body hb, as illustrated on a right side of FIG. 10. Then, the display unit 11 displays a tomographic image g21 obtained by rotating the tomographic image at the rotation angle θy about the Y axis, relative to the reference tomographic image, which is illustrated with a dotted line. The rotation angle θy is obtained by amplifying the actual rotation angle Δy γ times.

[Relationship Between Angle of Rotating about Z Axis and Tomographic Image]

Figure 11:
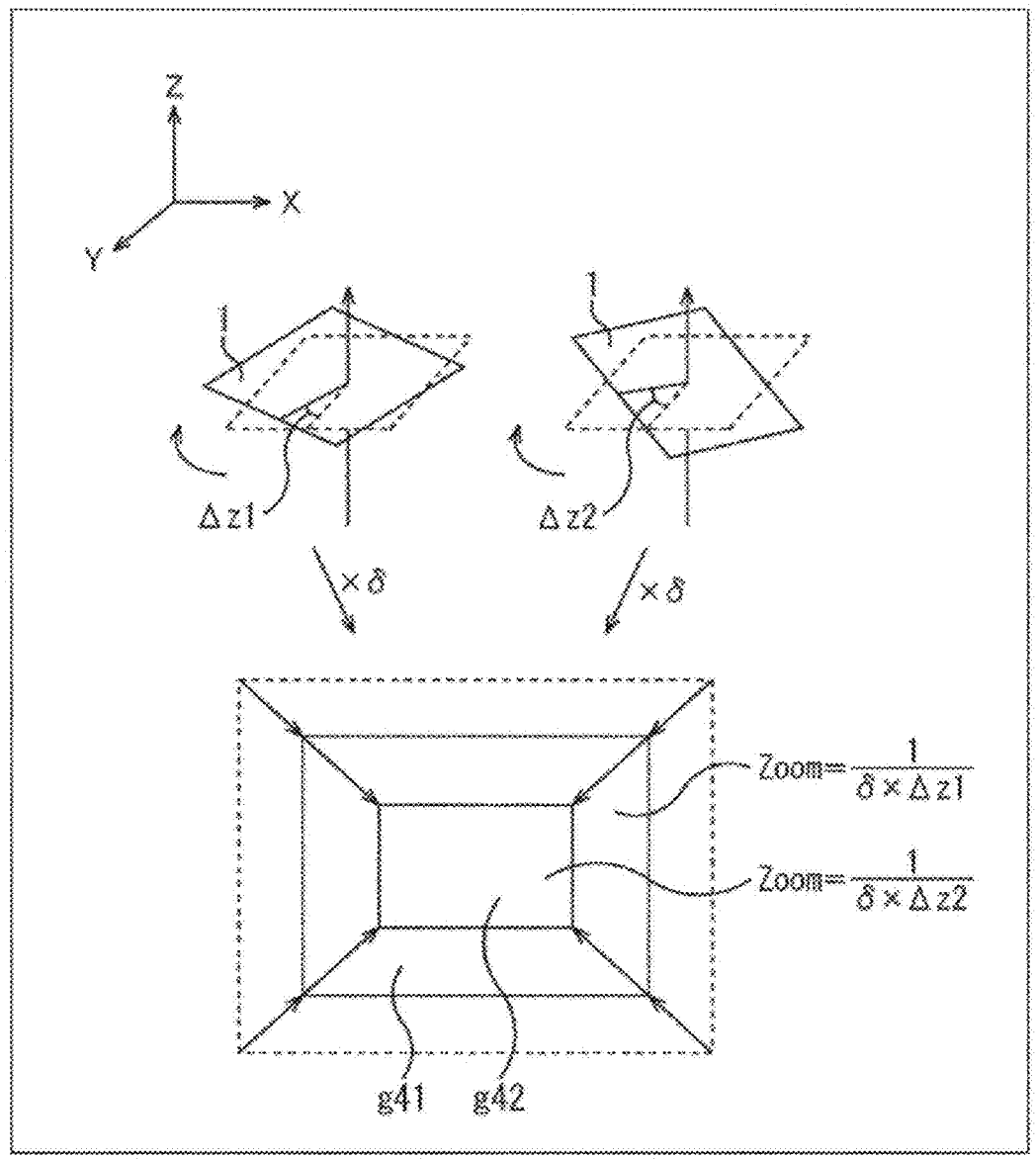
FIG. 11 is a diagram illustrating a relationship between an angle of rotating about a Z axis and the tomographic image.

FIG. 11 is a diagram illustrating the relationship between the angle of rotating the image processing device 1 about the Z axis and the tomographic image. Note that a rotation angle of rotating the image processing device 1, from a reference condition, about the Z axis is described as Δz.

As illustrated on an upper left side of FIG. 11, for example, it is presumed that the image processing device 1 is rotated clockwise at the rotation angle Δz=Δz1 about the Z axis, and the thus rotated image processing device 1 is pressed against the body hb.

Then, as illustrated in a lower side of FIG. 11, as compared with an angular field when imaging a reference tomographic image illustrated with a dotted line (hereinafter referred to as a reference angular field), an angular field when imaging an object to be examined (a range for the object to be examined to be shown in a tomographic image g41) is reduced by 1/(δ×Δz1) times in size. Note that a coefficient δ is a parameter for adjustment and an examiner can freely set and change the coefficient. In other words, the object to be examined which is zoomed in by (δ×Δz1) times is shown in the tomographic image g41.

Further, as illustrated in an upper right side of FIG. 11, for example, it is presumed that the image processing device 1 is rotated clockwise about the Z axis, and with the rotation angle being Δz=Δz2(>Δz1), the thus rotated image processing device 1 is pressed against the body hb.

Then, as illustrated in a lower side of FIG. 11, as compared with the reference angular field, an angular field when imaging the object to be examined (the range for the object to be examined to be shown in a tomographic image g42) is further reduced by 1/(δ×Δz2) times in size. In other words, the object to be examined which is further zoomed in by (δ×Δz2) times is shown in the tomographic image g42.

Reversely, although not shown, it is presumed that the image processing device 1 is rotated at the rotation angle Δz counterclockwise about the Z axis, and the thus rotated image processing device is pressed against the body hb.

Then, as compared with the reference angular field, an angular field when imaging the object to be examined (the range for the object to be examined to be shown in the tomographic image) is increased by (δ×Δz) times. In other words, the object to be examined which is zoomed out by 1/(δ×Δz) times is shown in the tomographic image.

The sensor information acquisition unit 63 acquires the rotation angles of the image processing device 1 as one of types of sensor information and stores the sensor information in the sensor information storage unit 54. Then, if the rotation is clockwise, the tomographic image generation unit 64 substitutes the rotation angle about the Z axis out of this rotation angles for an input parameter Δz to calculate the following formula (4). Alternatively, the tomographic image generation unit 64 calculates the following formula (5) if the rotation is counterclockwise. Accordingly, a change rate (hereinafter referred to as a zoom ratio) Zoom of a size of an angular field relative to a reference angular field is acquired.

$$Zoom = 1/(\delta \times \Delta z) \quad (4)$$

$$Zoom = (\delta \times \Delta z) \quad (5)$$

Then, the tomographic image generation unit 64 generates data of a tomographic image that shows the object to be examined with an angular field whose size has been changed by Zoom times relative to the reference angular field. In other words, the tomographic image generation unit 64 generates data of a zoomed-in or zoomed-out tomographic image.

Figure 12:
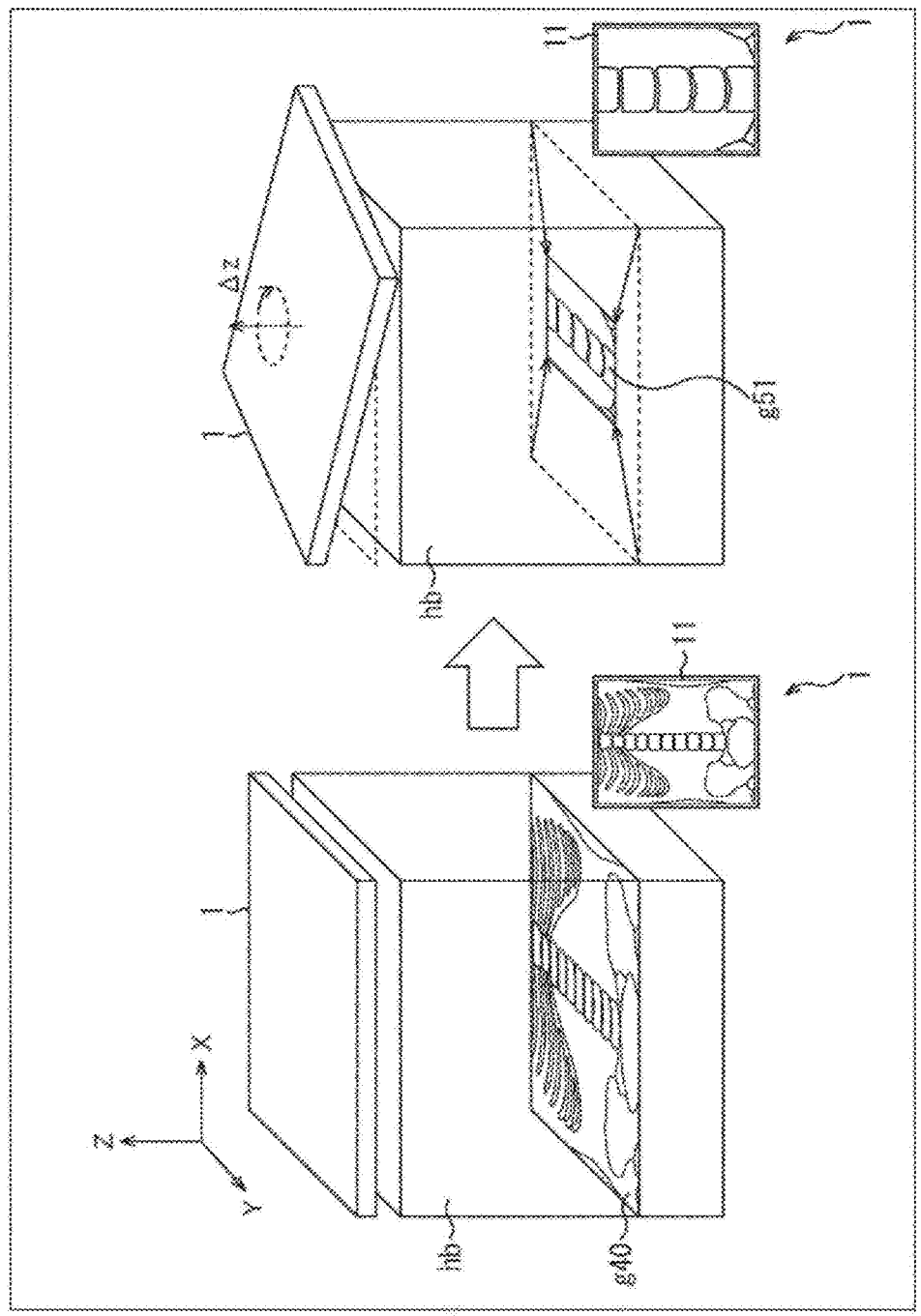
FIG. 12 is a diagram specifically illustrating a process result.

FIG. 12 is a diagram specifically illustrating a process result of FIG. 11.

As illustrated in a left side of FIG. 11, when the image processing device 1 with the reference angular field is pressed against the predetermined position of the body hb, the display unit 11 displays a reference tomographic image g40.

It is presumed that, from this condition, as illustrated in a right side of FIG. 12, the image processing device 1 is rotated clockwise at the rotation angle Δz about the Z axis, and the thus rotated image processing device 1 is pressed against the body hb. Then, the display unit 11 displays a tomographic image g51 whose size is reduced by 1/(δ×Δz) times relative to the reference angular field illustrated with a dotted line.

It is preferable if image correction is made such that even if the image processing device 1 is rotated, the tomographic image displayed on the display unit 11 is not rotated. This is because, if the tomographic image is rotated along with the rotation of the image processing device 1, it becomes difficult to perform the ultrasonic examination.

As has been described, an examiner performs an intuitive and simplified operation such as changing the pressure P and the rotation angles Δx, Δy, and Δz in pressing the image processing device 1 against the body hb. By performing the operation, the tomographic image displayed on the display unit 11 can be easily switched.

[Variation]

In the above-described embodiment, to switch a tomographic image displayed on the display unit 11, an examiner has changed the pressure P and the rotation angles Δx, Δy, and Δz in pressing the image processing device 1 against the body hb. However, a method for switching the tomographic image displayed on the display unit 11 is not limited to the above-described embodiment. Alternatively, for example, the tomographic image may be switched by an operation on a touch panel by the examiner when the touch panel laminated all over a display screen of the display unit 11 is adopted as an input unit 52 of the image processing device 1.

More specifically, although not shown, the input unit 52 configured as the touch panel is laminated all over the display screen of the display unit 11, detects coordinates of a position where a touch operation is made, and feeds a detection result thereof to a tomographic image generation unit 64. Note that the touch operation means contacting the touch panel with an object (for example, a finger of a user and a stylus pen) or a similar operation. The tomographic image generation unit 64 acquires the coordinates of the position of the touch panel where a touch operation is made as parameters, and transforms the reference tomographic image according to a change of the parameters to generate the tomographic image of the object to be displayed on the display unit 11.

[Operation with Touch Panel]

Figure 13:
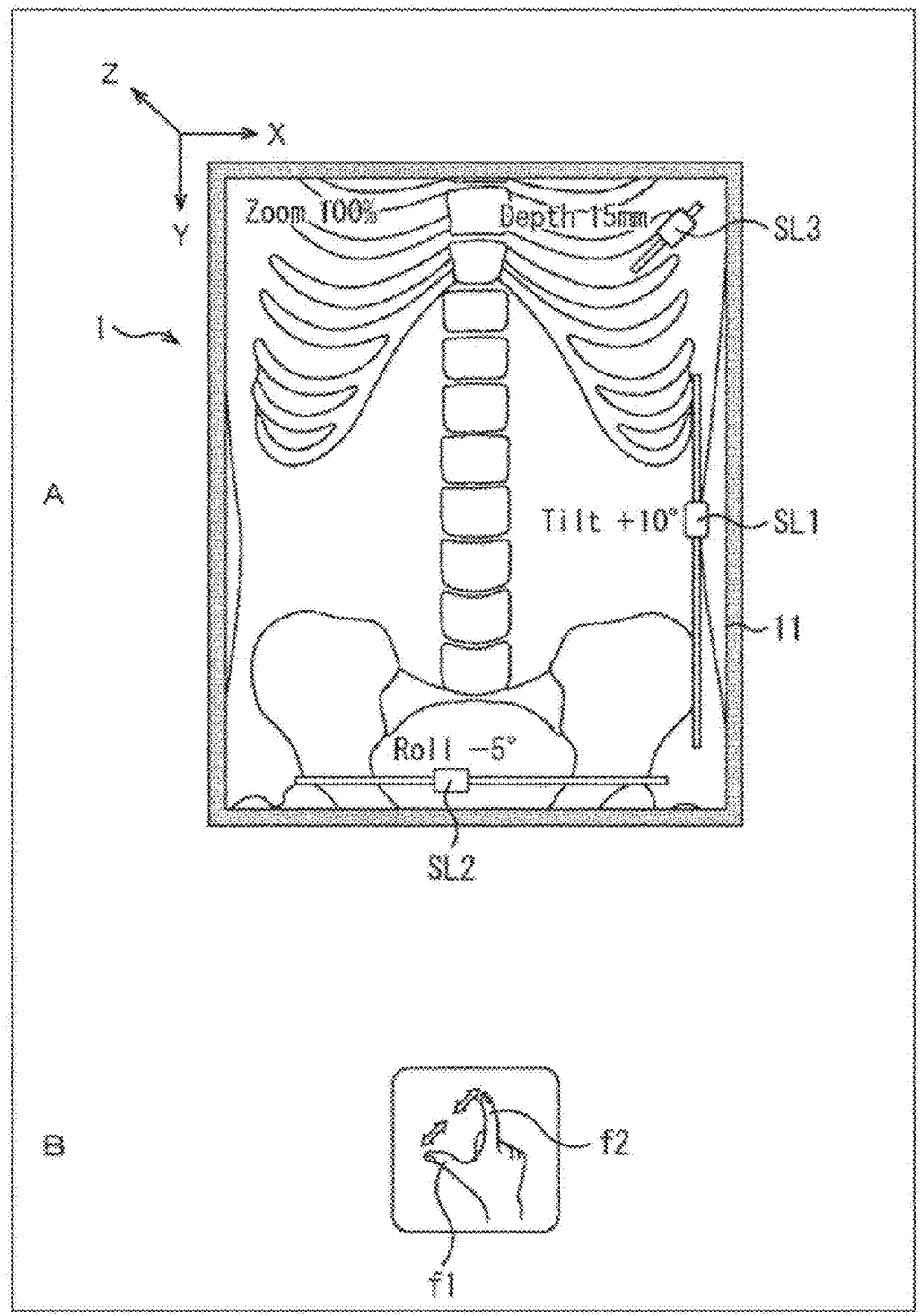
FIG. 13 is a diagram illustrating an exemplary display screen when an operation is made on a touch panel.

FIG. 13 is a diagram illustrating an example of a display screen when an operation is made through a touch panel.

As illustrated in FIG. 13A, in an area near a right surface side on the display unit 11, a slider SL1 for changing a rotation angle θx for rotating a tomographic image about an X axis is provided. Further, in an area near a lower surface side of the display unit 11, a slider SL2 for changing a rotation angle θy for rotating the tomographic image about a Y axis is provided. Furthermore, in an upper right area of the display unit 11, a slider SL3 for changing a distance in a Z axis direction of the tomographic image, that is, a depth D of a viewpoint is provided.

Specifically, with respect to the slider SL1, a center position corresponds to a rotation angle θx=0, and the upper the slider is positioned, for example, the larger the clockwise rotation angle θx, and the lower the slider is positioned, for example, the larger the counterclockwise rotation angle θx. Note that, according to an operation of the slider SL1, the rotation angle θx of the tomographic image is displayed near the slider SL1. From "Tilt +10°" displayed in the example of FIG. 13, it may be understood that the display unit 11 displays the tomographic image rotated clockwise at the rotation angle θx=10 degrees about the X axis, relative to the reference tomographic image.

With respect to the slider SL2, a center position corresponds to a rotation angle θy=0, and the further right the slider is positioned, for example, the larger the clockwise rotation angle θy. The further left the slider is positioned, for example, the larger the counterclockwise rotation angle θy. Note that, according to an operation of the slider SL2, the rotation angle θy of the tomographic image is displayed near the slider SL2. From "Roll −5°" displayed in the example of FIG. 13, it may be understood that the display unit 11 displays the tomographic image rotated counterclockwise at the rotation angle θy=5 degrees about the Y axis, relative to the reference tomographic image.

With respect to the slider SL3, an upper right position corresponds to a viewpoint depth D=0, and the further lower left the slider is positioned, the larger the viewpoint depth D. Note that, according to an operation of the slider SL3, the viewpoint depth D of the tomographic image is displayed near the slider SL3. From "Depth 15 mm" displayed in the example of FIG. 13, it may be understood that the display unit 11 displays the tomographic image of the viewpoint depth D=15 mm.

As illustrated in FIG. 13B, the examiner places two fingers f1 and f2 on the touch panel to perform a touch operation of widening or narrowing a space between the fingers f1 and f2 (hereinafter, such touch operation is referred to as a pinch operation). Accordingly, zoom-in and zoom-out of the tomographic image displayed on the display unit 11 can be instructed. That is, the pinch operation can be adopted alternatively, as the above-described operation for rotating the image processing device 1 about the Z axis.

Specifically, the pinch operation of widening the space between the fingers f1 and f2 leads to zoom-in of the tomographic image. Reversely, the pinch operation of narrowing the space between the fingers f1 and f2 leads to zoom-out of the tomographic image. Thus, according to the pinch operation, a zoom ratio of the tomographic image is displayed on an upper left area of the display unit 11. From "Zoom 100%" displayed in the example of FIG. 13, it may be understood that the display unit 11 displays the tomographic image whose zoom ratio is 100%.

[Another Example of Operation Through Touch Panel]

Figure 14:
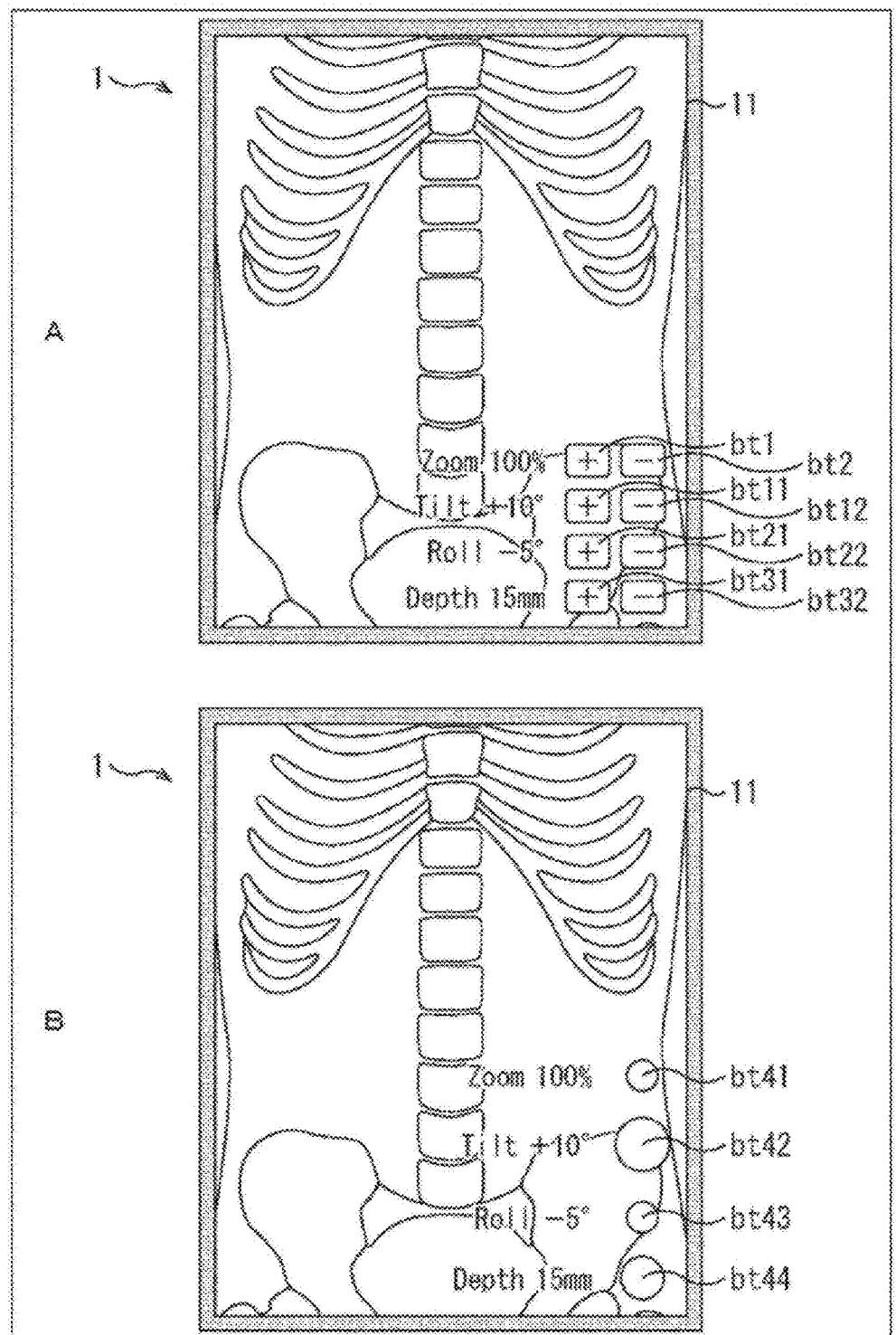
FIG. 14 is a diagram illustrating another example of the display screen when the operation is made on the touch panel.

FIG. 14 is a diagram illustrating another example of a display screen when an operation is performed though a touch panel.

FIG. 14A illustrates an example of switching display of a tomographic image according to the number of times a button is pressed.

As illustrated in FIG. 14A, at a lower right area of the display unit 11, software buttons bt1, bt2, software buttons bt11, bt12, software buttons bt21, bt22 and software buttons bt31, bt32 are arrayed. The software buttons bt1 and bt2 serve to change a zoom ratio of the tomographic image. The software buttons bt11 and bt12 serve to change a rotation angle θx for rotating the tomographic image about an X axis. The software buttons bt21 and bt22 serve to change a rotation angle θy for rotating the tomographic image about a Y axis. The software buttons bt31 and bt32 serve to change a distance in a Z axis direction of the tomographic image, that is, a viewpoint depth D.

Specifically, as the number of times the software button bt1 is pressed is increased, the zoom ratio becomes large. Reversely, as the number of times the software button bt2 is pressed is increased, the zoom ratio becomes small. Thus, the zoom ratio of the tomographic image is changed according to the number of times the software button bt1 or bt2 is pressed, and such zoom ratio of the tomographic image is displayed at a left side of the software button bt1.

Additionally, as the number of times the software button bt11 is pressed is increased, for example, a clockwise rotation angle θx becomes large. Reversely, as the number of times the software button bt12 is pressed is increased, for example, the clockwise rotation angle θx becomes small. Thus, the rotation angle θx of the tomographic image is changed according to the number of times the software button bt11 or bt12 is pressed, and such rotation angle θx of the tomographic image is displayed at a left side of the software button bt11.

Further additionally, as the number of times the software button bt21 is pressed is increased, for example, a clockwise rotation angle θy becomes large. Reversely, as the number of times the software button bt22 is pressed is increased, for example, the clockwise rotation angle θy becomes small. Thus, the rotation angle θy of the tomographic image is changed according to the number of times the software button bt21 or bt22 is pressed, and such rotation angle θy of the tomographic image is displayed at a left side of the software button bt21.

Still further, as the number of times the software button bt31 is pressed is increased, the viewpoint depth D becomes large. Reversely, as the number of times the software button bt32 is pressed is increased, the viewpoint depth D is approximated to zero. Thus, the viewpoint depth D of the tomographic image is changed according to the number of times the software button bt31 or bt32 is pressed, and such viewpoint depth D of the tomographic image is displayed at a left side of the software button bt31.

FIG. 14B is a diagram illustrating an example of switching display of the tomographic image according to how long a button is pressed.

As illustrated in FIG. 14B, at a lower right area of the display unit 11, software buttons bt41, bt42, bt43, and bt44 are arrayed. The software button bt41 serves to change a zoom ratio of the tomographic image. The software button bt42 serves to change a rotation angle θx for rotating the tomographic image about an X axis. The software button bt43 serves to change a rotation angle θy for rotating the tomographic image about a Y axis. The software button bt44 serves to change a distance in a Z axis direction of the tomographic image, that is, a viewpoint depth D.

Specifically, the longer the pressing time of the software button bt41, the larger the zoom ratio. If the zoom ratio reaches a pre-set maximum value, the zoom ratio is switched to a pre-set minimum value. Thus, the zoom ratio of the tomographic image is changed according to the pressing time of the software button bt41, and such zoom ratio of the tomographic image is displayed at a left side of the software button bt41.

Similarly, the longer the pressing time of the software button bt42, for example, the larger the clockwise rotation angle θx. If the clockwise rotation angle θx reaches a pre-set maximum value, the rotation angle is switched to a minimum value of the clockwise rotation angle θx. Thus, the rotation angle θ of the tomographic image is changed according to the pressing time of the software button bt42, and such rotation angle θ of the tomographic image is displayed at a left side of the software button bt42.

Further similarly, the longer the pressing time of the software button bt43, for example, the larger the clockwise rotation angle θy. If the clockwise rotation angle θy reaches a pre-set maximum value, the clockwise rotation angle θy is switched to a minimum value. Thus, the rotation angle θ of the tomographic image is changed according to the pressing time of the software button bt43, and such rotation angle θ of the tomographic image is displayed at a left side of the software button bt43.

Still further similarly, the longer the pressing time of the software button bt44, the larger the viewpoint depth D. If the viewpoint depth D reaches a pre-set maximum value, the viewpoint depth is switched to a minimum value of the viewpoint depth D, that is, 0 mm. Thus, the viewpoint depth D of the tomographic image is changed according to the pressing time of the software button bt44, and such viewpoint depth D of the tomographic image is displayed at a left side of the software button bt44.

Note that the software buttons bt41 to bt44 may be displayed in such a manner that a radius of a circle becomes large in proportion to the pressing time.

[Method for Displaying Tomographic Image]

Note that a method for displaying a tomographic image on the display unit 11 is not particularly limited. Hereinafter, an example of the method for displaying the tomographic image is described by referring to FIGS. 15 and 16.

Figure 15:
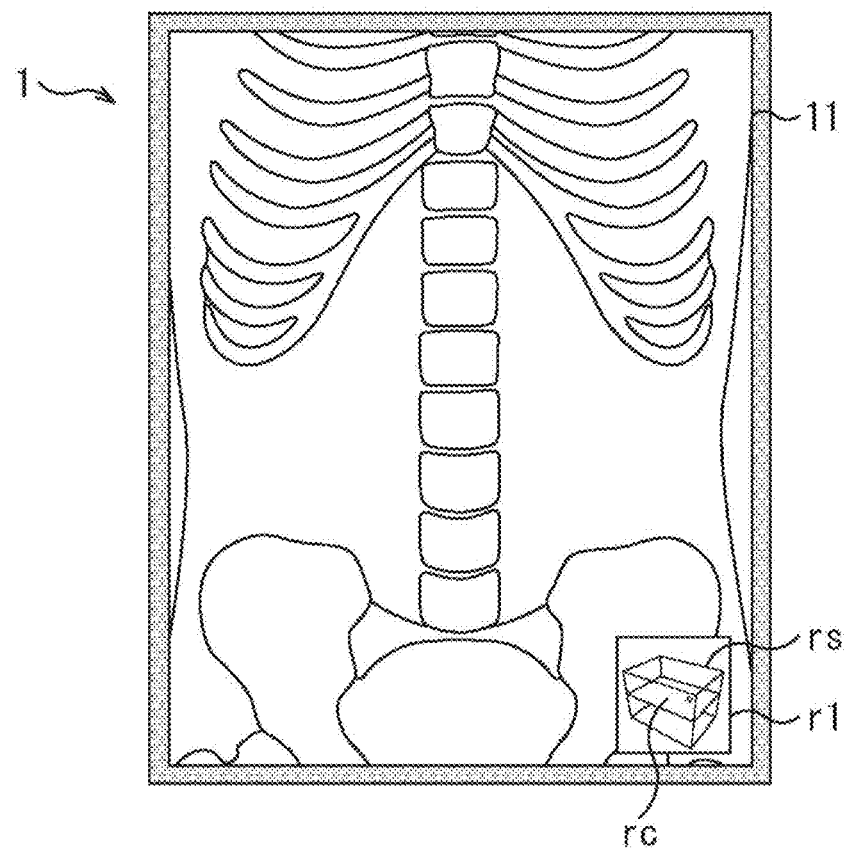
FIG. 15 is a diagram illustrating a display example of the tomographic image.

FIG. 15 is a diagram illustrating a display example of the tomographic image.

In an example of FIG. 15, the display unit 11 displays, on the entire screen, the tomographic image as a main image and displays, at a lower right edge, a sub-image r1 such that the sub-image r1 overlaps the main image. The sub-image indicates which position of the body hb is shown as a cross-section in the tomographic image. A cuboid rs included in the sub-image r1 indicates a portion of the body hb immediately below the image processing device 1. A plain surface rc displayed in the cuboid rs indicates a position of the cross-section of the body hb shown in the tomographic image displayed on the display unit 11.

Thus, an examiner views the sub-image r1 to intuitively grasp which cross-section in the body corresponds to a region shown in the main image (that is, the tomographic image).

Figure 16:
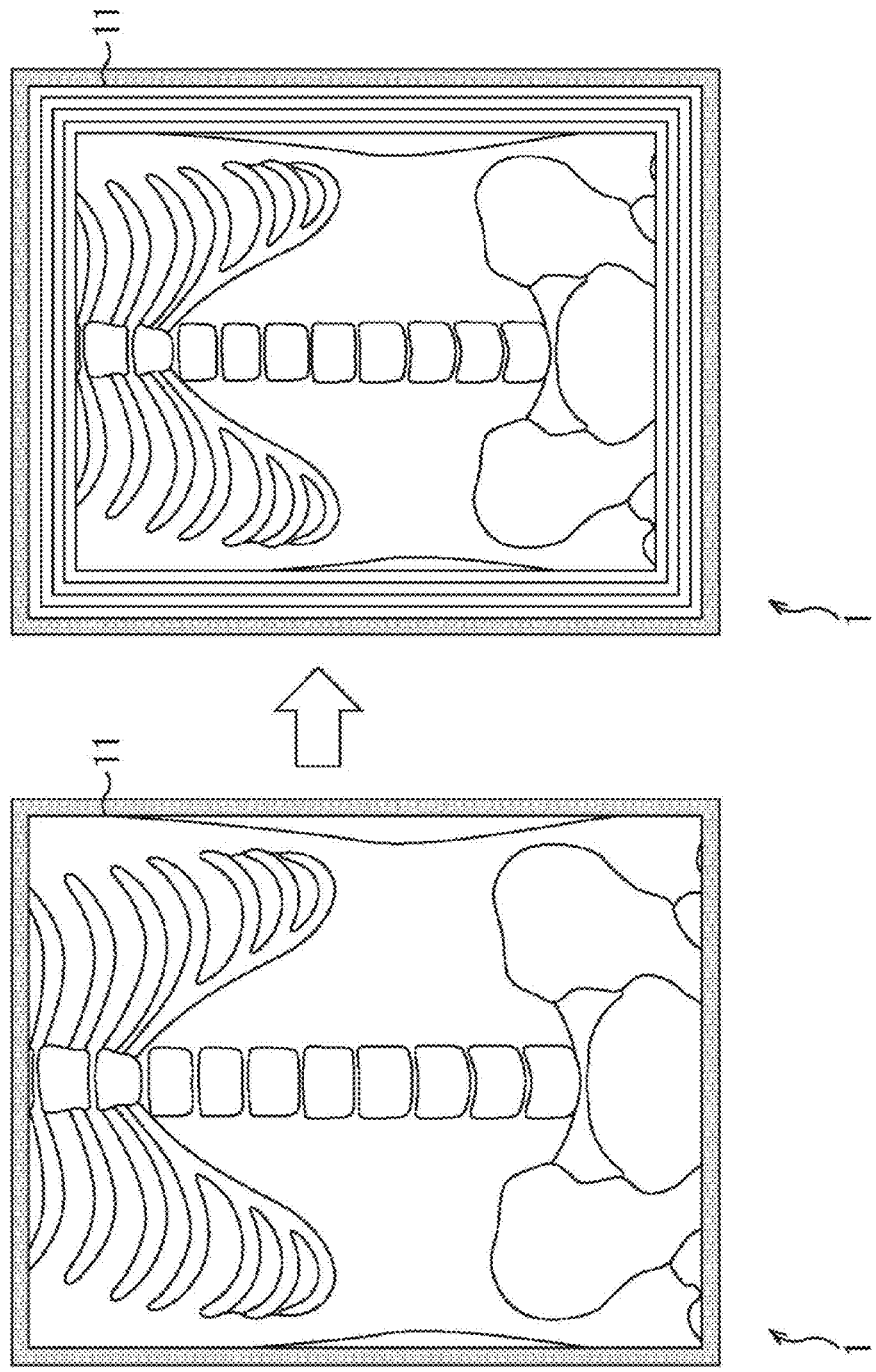
FIG. 16 is a diagram illustrating another display example of the tomographic image.

FIG. 16 is a diagram illustrating another display example of the tomographic image.

In an example of FIG. 16, according to a viewpoint depth D of the tomographic image, a display size relative to the display unit 11, that is, occupancy of the tomographic image in the whole screen of the display unit 11 is changed. Specifically, the shallower the viewpoint depth D of the tomographic image, the larger the occupancy of the tomographic image in the display unit 11. Thus, at a left side of FIG. 16, the tomographic image whose viewpoint depth D is the shallowest, that is, the tomographic image displayed all over the screen of the display unit 11 is illustrated. From this, as illustrated at a right side of FIG. 16, if the viewpoint depth D of the tomographic image is deepened, the occupancy of the tomographic image in the display unit 11 is lowered. That is, a relative display size of the tomographic image on the display unit 11 is reduced.

In summary, as a feature of a person in viewing an object, when the person views a near object, the object is recognized to be relatively large. On the other hand, when the person views a far object, the object is recognized to be relatively small. A natural law of perspective is a method that takes in such feature as a composition of painting and picture. Such method is also applied to the example of FIG. 16. Thus, the examiner can grasp an imaging position in the body more intuitively.

In the above-described display processes of an ultrasonic examination result, an examiner may select either one of a first mode and a second mode by switching. The first mode uses sensor information to change the tomographic image. The second mode directly displays a three-dimensional ultrasonic image of an object in the body hb that is immediately below an area where the probe 12 is pressed. If the second mode is adopted, a display control unit 65 controls the display unit 11 to display the three-dimensional ultrasonic image of the object in the body hb that is immediately below the area where the probe 12 is pressed, based on data of the three-dimensional ultrasonic image stored in the ultrasonic image 53.

As has been described, in the above-described example, data of the tomographic image has been generated according to both a pressure change when the image processing device 1 is pressed against the body hb and a change of a rotation angle of the image processing device 1 about the X axis, Y axis, and Z axis. However, each of the pressure change and the change of the rotation angle is an independent element for generation of the data of the tomographic image. Thus, either one of the elements may be used to generate the tomographic image.

Further, in the above-described example, the image processing device 1 is configured by physically integrating the probe 12 and the housing 1C that includes the display unit 11. However, if wired or wireless connection is electrically made between the housing 1C and the probe 12, a physical positional relationship is not particularly limited. For example, the probe 12 may be physically separated from the housing 1C. In this case, while an examiner holds the probe 12 to make an examination, a subject may hold the housing 1C to observe the tomographic image displayed on the display unit 11.

Alternatively, the data of the tomographic image imaged by the image processing device 1 may be transferred to another information processing device so that a display unit of the other information processing device displays the tomographic image. In this case, a method for transferring the data of the tomographic image is not particularly limited.

In the above-described example, the image processing device 1 displays the tomographic image in real time while imaging an ultrasonic image. However, each of imaging the ultrasonic image and generating the data of the tomographic image is an independent process. Thus, the image processing device 1 may generate the data of the tomographic image separately after recording the ultrasonic image. Specifically, the image processing device 1 may image a whole of the ultrasonic image in advance, and thereafter, at any timing, may display the tomographic image. In this case, if the data of the ultrasonic image is stored together with sensor information by the image processing device 1, a person who images the ultrasonic image and an examiner who makes an ultrasonic examination may be different persons. For example, even if the examiner is present in a place remote from a place where a subject is present, the examiner can freely view the tomographic image of any position in the body of the subject after imaging the ultrasonic image. As a result, as a part of a remote medical care, an appropriate ultrasonic examination can be realized.

Note that the present technique can be used for both a medical care purpose and a non-medical care purpose. Examples of the non-medical care purpose include health control. In this case, it is preferable if a frequency and intensity of an ultrasonic wave can be appropriately adjusted.

Further, the present technique can be widely used not only for a human, but also for, for example, an animal, a plant, and an artifact when imaging a cross-section of an object with the ultrasonic wave.

[Application of Present Technique to Program]

The above-described series of processes can be performed by hardware, and can also be performed by software. When the series of processes is to be performed by software, the programs that form the software are installed into a computer. Here, the computer may be a computer incorporated into special-purpose hardware, or may be a general-purpose personal computer that can execute various kinds of functions by installing various kinds of programs thereto.

Figure 17:
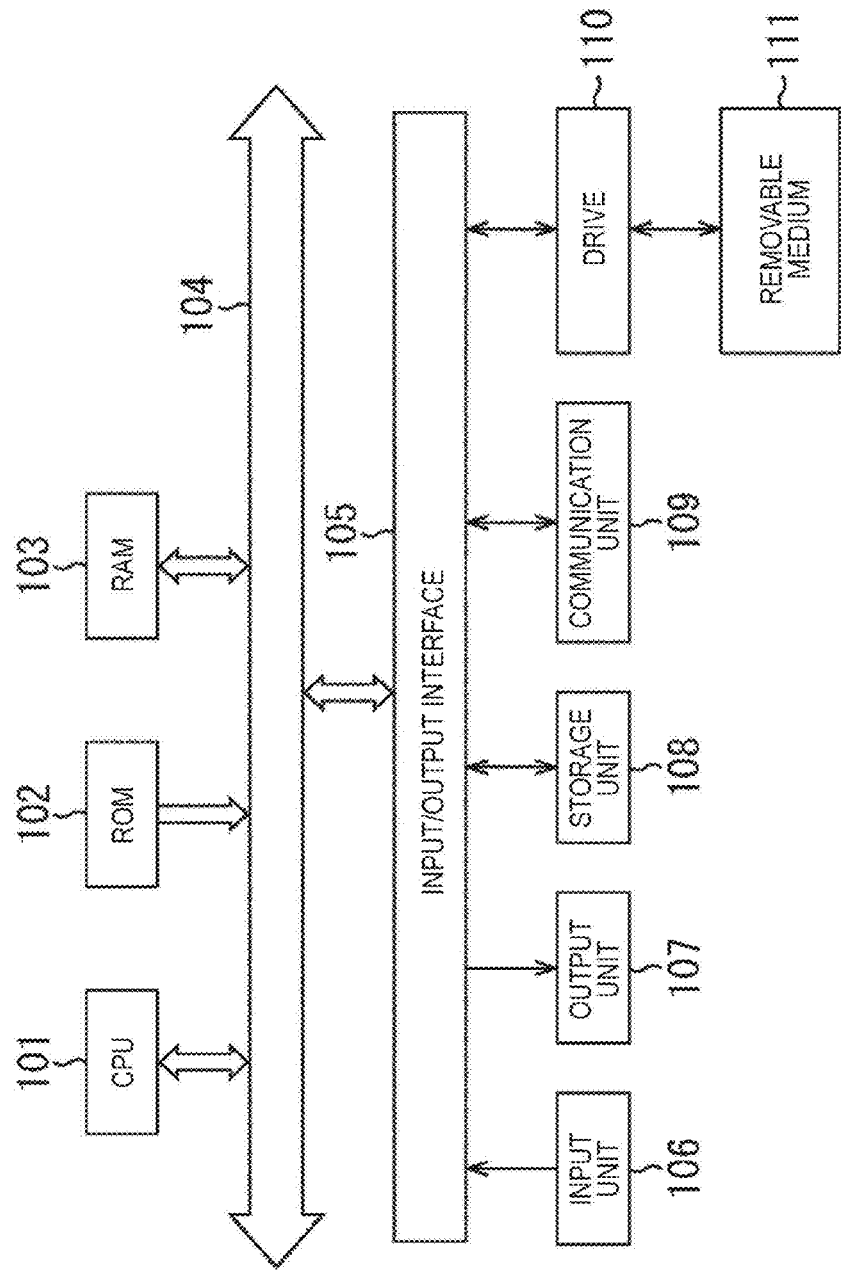
FIG. 17 is a block diagram illustrating an exemplary configuration of hardware of the image processing device to which the present technique is applied.

FIG. 17 is a block diagram illustrating an exemplary structure of the hardware of a computer that performs the above-described series of operations in accordance with a program.

In the computer, a central processing unit (CPU) 101, a read only memory (ROM) 102, and a random access memory (RAM) 103 are connected to one another by a bus 104.

An input/output interface 105 is further connected to the bus 104. An input unit 106, an output unit 107, a storage unit 108, a communication unit 109, and a drive 110 are connected to the input/output interface 105.

The input unit 106 is formed with a keyboard, a mouse, a microphone and the like. The output unit 107 is formed with a display, a speaker and the like. The storage unit 108 is formed with a hard disk, a nonvolatile memory or the like. The communication unit 109 is formed with a network interface or the like. The drive 110 drives a removable medium 111 such as a magnetic disk, an optical disk, a magnetooptical disk, or a semiconductor memory.

In the computer having the above-described structure, the CPU 101 loads a program stored in the storage unit 108 into the RAM 103 via the input/output interface 105 and the bus 104, and executes the program, so that the above-described series of operations is performed.

The programs to be executed by the computer (CPU 101) may be recorded on the removable medium 111 as a package medium to be provided, for example. Alternatively, the programs can be provided via a wired or wireless transmission medium such as a local area network, the Internet, or digital satellite broadcasting.

In the computer, the programs can be installed into the storage unit 108 via the input/output interface 105 when the removable medium 111 is mounted on the drive 110. The program can also be received by the communication unit 109 via a wired or wireless transmission medium, and be installed into the storage unit 108. Also, the program may be installed beforehand into the ROM 102 or the storage unit 108.

The programs to be executed by the computer may be programs for performing processes in chronological order in accordance with the sequence described in this specification, or may be programs for performing processes in parallel or performing a process when necessary, such as when there is a call.

It should be noted that embodiments of the present technique are not limited to the above-described embodiment, and various modifications may be made to it without departing from the scope of the present technique.

For example, the present technique can be embodied in a cloud computing structure in which one function is shared among apparatuses via a network, and processing is performed by the apparatuses which cooperate with one another.

The respective steps described with reference to the above-described flowcharts can be carried out by one apparatus or can be shared among apparatuses.

In a case where more than one process is included in one step, the processes included in the step can be performed by one apparatus or can be shared among apparatuses.

The present technique may also be embodied in the structures described below.

(1)

An image processing device including:

a probe that generates an ultrasonic wave and receives a reflective wave reflected at an object;

a sensor unit that detects one or more physical quantities of the probe;

a display unit that displays a tomographic image showing a cross-section of a predetermined position of the object based on the reflective wave received by the probe;

a tomographic image generation unit that generates the tomographic image to be displayed on the display unit by regarding sensor information detected by the sensor unit as a parameter and by transforming a reference tomographic image according to a change of the parameter; and a display control unit that controls the display unit to display the tomographic image generated by the tomographic image generation unit.

(2)

The image processing device according to (1) above, wherein the tomographic image generation unit uses at least a part of the sensor information as an input parameter to calculate a predetermined function, obtains accordingly at least one of variable elements of a depth, a rotation angle, and a zoom ratio of the tomographic image, and transforms the reference tomographic image by use of the variable element to generate the tomographic image to be displayed.

(3)

The image processing device according to (1) or (2) above, wherein the sensor unit detects pressure applied by the probe as the sensor information, and the tomographic image generation unit associates a change of the pressure with a change in a depth from a predetermined position of the object to generate the tomographic image.

(4)

The image processing device according to any one of (1) to (3) above, wherein the tomographic image generation unit generates the tomographic image such that the stronger the pressure of the probe, the deeper the depth of the tomographic image from the predetermined position of the object.

(5)

The image processing device according to any one of (1) to (4) above, wherein the sensor unit detects a rotation angle of the probe as the sensor information, and the tomographic image generation unit associates a change in the rotation angle with the rotation angle and/or the zoom ratio of the tomographic image to generate the tomographic image.

(6)

The image processing device according to any one of (1) to (5) above, wherein the sensor information includes each rotation angle of an X axis, a Y axis, and a Z axis, as the rotation angle, and the tomographic image generation unit associates a change in the rotation angle of the X axis with the rotation angle of the X axis of the tomographic image, associates a change in the rotation angle of the Y axis with the rotation angle of the Y axis of the tomographic image, and associates a change in the rotation angle of the Z axis with the zoom ratio of the tomographic image to generate the tomographic image.

(7)

The information processing device according to any one of (1) to (6) above, wherein the tomographic image generation unit generates the tomographic image such that the larger the rotation angle of the X axis or the rotation angle of the Y axis, the larger the rotation angle of the tomographic image.

(8)

The information processing device according to any one of (1) to (7) above, wherein the tomographic image generation unit generates the tomographic image such that the larger the rotation angle of the Z axis, the larger the zoom ratio of the tomographic image.

(9)

The image processing device according to any one of (1) to (8) above, wherein the tomographic image generation unit obtains information on a touch operation on a touch panel as a parameter, transforms the reference tomographic image by associating the transformation with the change of the parameter to generate the tomographic image to be displayed on the display unit.

(10)

An image processing method to be performed by an image processing device that includes a probe that generates an ultrasonic wave and receives a reflective wave reflected at an object, the method including the steps of:

detecting one or more physical quantities of the probe;

displaying a tomographic image showing a cross-section of a predetermined position of the object based on the reflective wave received by the probe;

generating the tomographic image to be displayed by regarding detected sensor information as a parameter and transforming a reference tomographic image according to a change of the parameter; and controlling to display the generated tomographic image.

(11)

A program readable by a computer that controls an image processing device that includes a probe that generates an ultrasonic wave and receives a reflective wave reflected at an object, the program causing the computer to execute the steps of:

detecting one or more physical quantities of the probe;

displaying a tomographic image showing a cross-section of a predetermined position of the object based on the reflective wave received by the probe;

generating the tomographic image to be displayed by regarding detected sensor information as a parameter and transforming a reference tomographic image according to a change of the parameter; and controlling to display the generated tomographic image.

The present technique can be applied to an ultrasonic examination device.

REFERENCE SIGNS LIST

1 Image processing device
1C Housing
11 Display unit
12 Probe
21 Ultrasonic wave transmission/reception unit
22 Detection unit
31 Ultrasonic wave generation unit
32 Ultrasonic wave reception unit
41 Acceleration sensor
42 Angular velocity sensor
43 Geomagnetic sensor
44 Pressure sensor
51 Main control unit
52 Input unit
53 Ultrasonic image storage unit
54 Sensor information storage unit
55 Tomographic image storage unit
61 Ultrasonic wave control unit
62 Ultrasonic image generation unit
63 Sensor information acquisition unit
64 Tomographic image generation unit
65 Display control unit

The invention claimed is:

1. An image processing device, comprising:
a probe configured to:
 generate an ultrasonic wave; and
 receive a reflective wave reflected from an object;
a sensor unit configured to detect sensor information of the probe,
 wherein the sensor information indicates a pressure applied on a body that includes the object;
a tomographic image generation unit configured to:
 generate a first tomographic image, based on the sensor information and a reference tomographic image; and
 change a zoom ratio of the generated first tomographic image based on a first rotation angle of the probe; and
a display unit configured to:
 display the first tomographic image,
 wherein the displayed first tomographic image shows a cross-section view of inside of the body at a position of the object in the body, and
 wherein a depth of a viewpoint of the displayed first tomographic image is based on the pressure applied on the body; and
display a sub-image superimposed on a part of the displayed first tomographic image,
 wherein the sub-image indicates the position of the object in the body.

2. The image processing device according to claim 1, wherein the tomographic image generation unit is further configured to:
obtain at least one of the depth or a second rotation angle of the first tomographic image based on the sensor information; and
generate the first tomographic image, based on at least one of the depth, the second rotation angle, or the zoom ratio and the reference tomographic image.

3. The image processing device according to claim 1, wherein the tomographic image generation unit is further configured to change the depth of the viewpoint of the first tomographic image based on a change in the pressure applied on the body.

4. The image processing device according to claim 1, wherein the depth of the viewpoint of the first tomographic image changes from a first depth to a second depth, based on a change in the pressure applied on the body, from a first pressure to a second pressure,
wherein the first depth of the first tomographic image is greater than the second depth of the first tomographic image, and
wherein the first pressure applied by the probe on the body is greater than the second pressure applied on the body.

5. The image processing device according to claim 1,
wherein the sensor information further indicates the first rotation angle of the probe, and
wherein the tomographic image generation unit is further configured to change a second rotation angle of the first tomographic image based on the first rotation angle of the probe.

6. The image processing device according to claim 5,
wherein the first rotation angle of the probe comprises at least one of a third rotation angle of an X axis of the probe, or a fourth rotation angle of a Y axis of the probe, or a fifth rotation angle of a Z axis of the probe,
wherein the X axis, the Y axis, and the Z axis are mutually perpendicular;
wherein the tomographic image generation unit is further configured to:
 change a sixth rotation angle of the X axis of the first tomographic image based on the third rotation angle,
 change a seventh rotation angle of the Y axis of the first tomographic image based on the fourth rotation angle, and
 change the zoom ratio of the first tomographic image based on the fifth rotation angle.

7. The image processing device according to claim 6,
wherein the sixth rotation angle increases from a first value to a second value, based on increase of the third rotation angle from a third value to a fourth value, and
wherein the seventh rotation angle increases from a fifth value to a sixth value, based on increase of the fourth rotation angle from a seventh value to an eighth value.

8. The image processing device according to claim 6, wherein the zoom ratio of the first tomographic image increases from a first value to a second value, based on an increase of the fifth rotation angle from a third value to a fourth value.

9. The image processing device according to claim 1, wherein the tomographic image generation unit is further configured to generate the first tomographic image based on a touch operation on a touch panel.

10. The image processing device according to claim 1, wherein the tomographic image generation unit is further configured to change the zoom ratio based on one of a clockwise rotation or an anticlockwise rotation of the image processing device.

11. The image processing device according to claim 1, wherein the zoom ratio is changed to a minimum zoom value based on the zoom ratio that reaches a maximum zoom value.

12. The image processing device according to claim 1, wherein the display unit is further configured to display the sub-image at a lower right edge of the first tomographic image.

13. The image processing device according to claim 1, wherein the display unit is further configured to change a display size of the first tomographic image based on the depth of the viewpoint.

14. The image processing device according to claim 13, wherein the display size of the first tomographic image changes from a first size to a second size, based on a change in the depth of the viewpoint of the first tomographic image, from a first depth to a second depth,
wherein the first size of the first tomographic image is smaller than the second size of the first tomographic image, and
wherein the first depth of the first tomographic image is greater than the second depth of the first tomographic image.

15. An image processing method, comprising:
in an image processing device that includes a probe configured to generate an ultrasonic wave and receive a reflective wave reflected from an object:
detecting sensor information of the probe,
wherein the sensor information indicates a pressure applied on a body that includes the object;
generating a first tomographic image, based on the sensor information and a reference tomographic image;
changing a zoom ratio of the generated first tomographic image based on a rotation angle of the probe;
displaying the first tomographic image,
wherein the displayed first tomographic image shows a cross-section view of inside of the body at a position of the object in the body, and
wherein a depth of a viewpoint of the displayed first tomographic image is based on the pressure applied on the body; and
displaying a sub-image superimposed on a part of the displayed first tomographic image,
wherein the sub-image indicates the position of the object in the body.

16. A non-transitory computer-readable medium having stored thereon computer-executable instructions, which when executed by a computer, cause the computer to execute operations, the operations comprising:
in an image processing device that includes a probe configured to generate an ultrasonic wave and receive a reflective wave reflected from an object:
detecting sensor information of the probe,
wherein the sensor information indicates a pressure applied on a body that includes the object;
generating a first tomographic image, based on the sensor information and a reference tomographic image;
changing a zoom ratio of the generated first tomographic image based on a rotation angle of the probe; and
displaying the first tomographic image,
wherein the displayed first tomographic image shows a cross-section view of inside of the body at a position of the object in the body, and
wherein a depth of a viewpoint of the displayed first tomographic image is based on the pressure applied on the body; and
displaying a sub-image superimposed on a part of the displayed first tomographic image,
wherein the sub-image indicates the position of the object in the body.

* * * * *